(12) United States Patent
Ogdahl et al.

(10) Patent No.: US 8,777,837 B2
(45) Date of Patent: Jul. 15, 2014

(54) SURGICAL ARTICLES AND METHODS FOR TREATING PELVIC

(71) Applicant: AMS Research Corporation, Minnetonka, MN (US)

(72) Inventors: Jason W. Ogdahl, Minneapolis, MN (US); Jose W. Jimenez, Apple Valley, MN (US); Chaouki A. Khamis, Edina, MN (US); Jessica L. Roll, Maple Grove, MN (US); Michelle L. Solari, Minneapolis, MN (US); John F. Otte, St. Anthony, MN (US); Mona N. Dahdah, West St. Paul, MN (US)

(73) Assignee: AMS Research Corporation, Minnetonka, MN (US)

( * ) Notice: Subject to any disclaimer, the term of this patent is extended or adjusted under 35 U.S.C. 154(b) by 0 days.

(21) Appl. No.: 13/758,481

(22) Filed: Feb. 4, 2013

(65) Prior Publication Data

US 2013/0144115 A1 Jun. 6, 2013

Related U.S. Application Data

(63) Continuation of application No. 12/446,492, filed as application No. PCT/US2007/022675 on Oct. 26, 2007, now Pat. No. 8,388,514.

(60) Provisional application No. 60/934,051, filed on Jun. 11, 2007, provisional application No. 60/863,064, filed on Oct. 26, 2006.

(51) Int. Cl.
*A61F 2/00* (2006.01)

(52) U.S. Cl.
USPC ............................................ 600/37

(58) Field of Classification Search
USPC ......... 600/29–30, 37; 128/885; 606/151, 222, 606/139
See application file for complete search history.

(56) References Cited

U.S. PATENT DOCUMENTS

| | | | |
|---|---|---|---|
| 2,738,790 A | 3/1956 | Todt et al. |
| 3,472,232 A | 10/1969 | Earl |
| 3,580,313 A | 5/1971 | McKnight |
| 3,763,860 A | 10/1973 | Clarke |
| 3,858,783 A | 1/1975 | Kapitanov et al. |
| 3,995,619 A | 12/1976 | Glatzer |

(Continued)

FOREIGN PATENT DOCUMENTS

| | | |
|---|---|---|
| AU | 2002241673 | 11/2005 |
| CA | 2404459 | 8/2005 |

(Continued)

OTHER PUBLICATIONS

"We're staying ahead of the curve" Introducing the IVS Tunneller Device for Tension Free Procedures, Tyco Healthcare, 3 pages (2002).

(Continued)

*Primary Examiner* — Christine Matthews
(74) *Attorney, Agent, or Firm* — Kagan Binder, PLLC

(57) ABSTRACT

Described are devices, implants, insertion tools, combinations, and associated methods, that involve placement of a self-fixating tip at tissue of the pelvic region, wherein an insertion tool includes one or more of an aperture for engaging a guide and an extension guard, the method optionally allowing for initial placement of a self-fixating tip at tissue of the pelvic region and adjustment of the location of the self-fixating tip.

19 Claims, 9 Drawing Sheets

(56) References Cited

U.S. PATENT DOCUMENTS

| | | |
|---|---|---|
| 4,172,458 A | 10/1979 | Pereyra |
| 4,235,238 A | 11/1980 | Ogiu et al. |
| 4,441,497 A | 4/1984 | Paudler |
| 4,509,516 A | 4/1985 | Richmond |
| 4,548,202 A | 10/1985 | Duncan |
| 4,632,100 A | 12/1986 | Somers et al. |
| 4,873,976 A | 10/1989 | Schreiber |
| 4,932,962 A | 6/1990 | Yoon et al. |
| 4,938,760 A | 7/1990 | Burton et al. |
| 4,969,892 A | 11/1990 | Burton et al. |
| 4,979,956 A | 12/1990 | Silvestrini |
| 5,013,292 A | 5/1991 | Lemay |
| 5,013,316 A | 5/1991 | Goble et al. |
| 5,053,043 A | 10/1991 | Gottesman et al. |
| 5,085,661 A | 2/1992 | Moss |
| 5,112,344 A | 5/1992 | Petros |
| 5,141,520 A | 8/1992 | Goble et al. |
| 5,149,329 A | 9/1992 | Richardson |
| 5,188,636 A | 2/1993 | Fedotov |
| 5,203,864 A | 4/1993 | Phillips |
| 5,209,756 A | 5/1993 | Seedhom et al. |
| 5,234,438 A | 8/1993 | Semrad |
| 5,256,133 A | 10/1993 | Spitz |
| 5,268,001 A | 12/1993 | Nicholson et al. |
| 5,269,783 A | 12/1993 | Sander |
| 5,281,237 A | 1/1994 | Gimpelson |
| 5,328,077 A | 7/1994 | Lou |
| 5,337,736 A | 8/1994 | Reddy |
| 5,354,292 A | 10/1994 | Braeuer et al. |
| 5,368,595 A | 11/1994 | Lewis |
| 5,370,650 A | 12/1994 | Tovey et al. |
| 5,370,662 A | 12/1994 | Stone et al. |
| 5,376,097 A | 12/1994 | Phillips |
| 5,383,904 A | 1/1995 | Totakura et al. |
| 5,403,328 A | 4/1995 | Shallman |
| 5,439,467 A | 8/1995 | Benderev et al. |
| 5,474,518 A | 12/1995 | Farrer Velazquez |
| 5,474,543 A | 12/1995 | McKay |
| 5,520,700 A | 5/1996 | Beyar et al. |
| 5,520,703 A | 5/1996 | Essig |
| 5,527,342 A | 6/1996 | Pietrzak et al. |
| 5,544,664 A | 8/1996 | Benderev et al. |
| 5,562,689 A | 10/1996 | Green et al. |
| 5,571,139 A | 11/1996 | Jenkins, Jr. |
| 5,582,188 A | 12/1996 | Benderev et al. |
| 5,584,860 A | 12/1996 | Goble et al. |
| 5,591,163 A | 1/1997 | Thompson |
| 5,591,206 A | 1/1997 | Moufarrege |
| 5,611,515 A | 3/1997 | Benderev et al. |
| 5,628,756 A | 5/1997 | Barker, Jr. et al. |
| 5,643,320 A | 7/1997 | Lower et al. |
| 5,647,836 A | 7/1997 | Blake et al. |
| 5,669,935 A | 9/1997 | Rosenman et al. |
| 5,674,247 A | 10/1997 | Sohn |
| 5,683,349 A | 11/1997 | Makower et al. |
| 5,690,655 A | 11/1997 | Hart et al. |
| 5,697,931 A | 12/1997 | Thompson |
| 5,709,708 A | 1/1998 | Thal |
| 5,725,529 A | 3/1998 | Nicholson et al. |
| 5,725,541 A | 3/1998 | Anspach, III et al. |
| 5,741,282 A | 4/1998 | Anspach, III et al. |
| 5,782,862 A | 7/1998 | Bonuttie |
| 5,842,478 A | 12/1998 | Benderev et al. |
| 5,873,891 A | 2/1999 | Sohn |
| 5,899,909 A | 5/1999 | Claren et al. |
| 5,904,692 A | 5/1999 | Steckel et al. |
| 5,922,026 A | 7/1999 | Chin |
| 5,925,047 A | 7/1999 | Errico et al. |
| 5,944,732 A | 8/1999 | Raulerson et al. |
| 5,954,057 A | 9/1999 | Li |
| 5,972,000 A | 10/1999 | Beyar et al. |
| 5,980,558 A | 11/1999 | Wiley |
| 5,984,927 A | 11/1999 | Wenstrom, Jr. |
| 5,988,171 A | 11/1999 | Sohn et al. |
| 5,997,554 A | 12/1999 | Thompson |
| 6,007,539 A | 12/1999 | Kirsch et al. |
| 6,019,768 A | 2/2000 | Wenstrom et al. |
| 6,027,523 A | 2/2000 | Schmieding |
| 6,030,393 A | 2/2000 | Corlew |
| 6,036,701 A | 3/2000 | Rosenman |
| 6,042,583 A | 3/2000 | Thompson et al. |
| 6,048,351 A | 4/2000 | Gordon et al. |
| 6,053,935 A | 4/2000 | Brenneman et al. |
| 6,056,688 A | 5/2000 | Benderev et al. |
| 6,099,538 A | 8/2000 | Moses et al. |
| 6,099,551 A | 8/2000 | Gabby |
| 6,099,552 A | 8/2000 | Adams |
| 6,127,597 A | 10/2000 | Beyar et al. |
| 6,168,611 B1 | 1/2001 | Risvi |
| 6,200,330 B1 | 3/2001 | Benderev et al. |
| 6,241,736 B1 | 6/2001 | Sater et al. |
| 6,245,082 B1 | 6/2001 | Gellman et al. |
| 6,264,676 B1 | 7/2001 | Gellman et al. |
| 6,273,852 B1 | 8/2001 | Lehe et al. |
| 6,319,272 B1 | 11/2001 | Brenneman et al. |
| 6,322,492 B1 | 11/2001 | Kovac |
| 6,328,744 B1 | 12/2001 | Harari et al. |
| 6,334,446 B1 | 1/2002 | Beyar |
| 6,382,214 B1 | 5/2002 | Raz et al. |
| 6,387,041 B1 | 5/2002 | Harari et al. |
| 6,406,423 B1 | 6/2002 | Scetbon |
| 6,406,480 B1 | 6/2002 | Beyar et al. |
| 6,423,072 B1 | 7/2002 | Zappala |
| 6,423,080 B1 | 7/2002 | Gellman et al. |
| 6,440,154 B2 | 8/2002 | Gellman et al. |
| 6,451,024 B1 | 9/2002 | Thompson et al. |
| 6,454,778 B2 | 9/2002 | Kortenbach |
| 6,475,139 B1 | 11/2002 | Miller |
| 6,478,727 B2 | 11/2002 | Scetbon |
| 6,491,703 B1 | 12/2002 | Ulmsten |
| 6,502,578 B2 | 1/2003 | Raz et al. |
| 6,506,190 B1 | 1/2003 | Walshe |
| 6,530,943 B1 | 3/2003 | Hoepffner et al. |
| 6,544,273 B1 | 4/2003 | Harari et al. |
| 6,582,443 B2 | 6/2003 | Cabak et al. |
| 6,592,515 B2 | 7/2003 | Thierfelder |
| 6,592,610 B2 | 7/2003 | Beyar |
| 6,596,001 B2 | 7/2003 | Stormby et al. |
| 6,599,235 B2 | 7/2003 | Kovac |
| 6,602,260 B2 | 8/2003 | Harari et al. |
| 6,612,977 B2 | 9/2003 | Staskin |
| 6,635,058 B2 | 10/2003 | Beyar et al. |
| 6,638,210 B2 | 10/2003 | Berger |
| 6,641,525 B2 | 11/2003 | Rocheleau |
| 6,673,010 B2 | 1/2004 | Skiba et al. |
| 6,685,629 B2 | 2/2004 | Therin |
| 6,689,047 B2 | 2/2004 | Gellman et al. |
| 6,730,110 B1 | 5/2004 | Harari et al. |
| 6,746,455 B2 | 6/2004 | Beyar et al. |
| 6,752,814 B2 | 6/2004 | Gellman et al. |
| 6,802,807 B2 | 10/2004 | Anderson et al. |
| 6,884,212 B2 | 4/2005 | Thierfelder et al. |
| 6,908,425 B2 | 6/2005 | Luscombe |
| 6,908,473 B2 | 6/2005 | Skiba et al. |
| 6,911,002 B2 | 6/2005 | Fierro |
| 6,911,003 B2 | 6/2005 | Anderson et al. |
| 6,932,759 B2 | 8/2005 | Kammerer |
| 6,936,052 B2 | 8/2005 | Gellman et al. |
| 6,971,986 B2 | 12/2005 | Staskin et al. |
| 6,974,462 B2 | 12/2005 | Sater |
| 6,981,983 B1 | 1/2006 | Rosenblatt et al. |
| 6,991,597 B2 | 1/2006 | Gellman et al. |
| 7,014,607 B2 | 3/2006 | Gellman |
| 7,025,772 B2 | 4/2006 | Gellman et al. |
| 7,037,255 B2 | 5/2006 | Inman |
| 7,048,682 B2 | 5/2006 | Neisz et al. |
| 7,056,333 B2 | 6/2006 | Walshe |
| 7,070,556 B2 | 7/2006 | Anderson |
| 7,083,637 B1 | 8/2006 | Tannhauser |
| 7,087,059 B2 | 8/2006 | Harari et al. |
| 7,112,171 B2 | 9/2006 | Rocheleau et al. |
| 7,121,997 B2 | 10/2006 | Kammerer et al. |
| 7,131,943 B2 | 11/2006 | Kammerer |
| 7,223,229 B2 | 5/2007 | Inman et al. |

(56) References Cited

U.S. PATENT DOCUMENTS

| | | |
|---|---|---|
| 7,226,407 B2 | 6/2007 | Kammerer |
| 7,226,408 B2 | 6/2007 | Harai et al. |
| 7,229,404 B2 | 6/2007 | Bouffier |
| 7,229,453 B2 | 6/2007 | Anderson |
| 7,235,043 B2 | 6/2007 | Gellman et al. |
| 7,261,723 B2 | 8/2007 | Smith et al. |
| 7,267,645 B2 | 9/2007 | Anderson et al. |
| 7,291,104 B2 | 11/2007 | Neisz et al. |
| 7,297,102 B2 | 11/2007 | Smith et al. |
| 7,303,525 B2 | 12/2007 | Watschke et al. |
| 7,326,213 B2 | 2/2008 | Benderev et al. |
| 7,347,812 B2 | 3/2008 | Mellier |
| 7,351,196 B2 | 4/2008 | Goldmann et al. |
| 7,351,197 B2 | 4/2008 | Montpetit et al. |
| 7,357,773 B2 | 4/2008 | Watschke et al. |
| 7,364,541 B2 | 4/2008 | Chu et al. |
| 7,371,245 B2 | 5/2008 | Evans et al. |
| 7,387,634 B2 | 6/2008 | Benderev |
| 7,393,320 B2 | 7/2008 | Montpetit et al. |
| 7,407,480 B2 | 8/2008 | Staskin |
| 7,410,460 B2 | 8/2008 | Benderev |
| 7,413,540 B2 | 8/2008 | Gellman et al. |
| 7,422,557 B2 | 9/2008 | Arnal |
| 7,494,495 B2 | 2/2009 | Delorme et al. |
| 7,500,945 B2 | 3/2009 | Cox |
| 7,517,313 B2 | 4/2009 | Thierfelder et al. |
| 7,527,588 B2 | 5/2009 | Zaddem et al. |
| 7,527,633 B2 | 5/2009 | Rioux |
| 7,547,316 B2 | 6/2009 | Priewe et al. |
| 7,588,598 B2 | 9/2009 | Delorme et al. |
| 7,601,118 B2 | 10/2009 | Smith et al. |
| 7,614,999 B2 | 11/2009 | Gellman et al. |
| 7,621,865 B2 | 11/2009 | Gellman et al. |
| 7,637,860 B2 | 12/2009 | MacLean |
| 7,686,759 B2 | 3/2010 | Sater |
| 7,686,760 B2 | 3/2010 | Anderson et al. |
| 7,691,050 B2 | 4/2010 | Gellman et al. |
| 7,691,052 B2 | 4/2010 | Gellman et al. |
| 7,740,576 B2 | 6/2010 | Hodroff |
| 7,753,839 B2 | 7/2010 | Siegel et al. |
| 7,762,942 B2 | 7/2010 | Neisz et al. |
| 7,828,715 B2 | 11/2010 | Haverfield |
| 2001/0000533 A1 | 4/2001 | Kovac |
| 2001/0018549 A1 | 8/2001 | Scetbon |
| 2001/0027321 A1 | 10/2001 | Gellman et al. |
| 2001/0041895 A1 | 11/2001 | Beyar et al. |
| 2001/0049467 A1 | 12/2001 | Lehe et al. |
| 2001/0053916 A1 | 12/2001 | Rioux |
| 2002/0007222 A1 | 1/2002 | Desai |
| 2002/0028980 A1 | 3/2002 | Thierfelder et al. |
| 2002/0035369 A1 | 3/2002 | Beyar et al. |
| 2002/0038119 A1 | 3/2002 | Weber et al. |
| 2002/0038132 A1 | 3/2002 | Abrams |
| 2002/0050277 A1 | 5/2002 | Beyar |
| 2002/0055748 A1 | 5/2002 | Gellman et al. |
| 2002/0058959 A1 | 5/2002 | Gellman et al. |
| 2002/0068948 A1 | 6/2002 | Stormby et al. |
| 2002/0077526 A1 | 6/2002 | Kammerer et al. |
| 2002/0082619 A1 | 6/2002 | Cabak et al. |
| 2002/0091373 A1 | 7/2002 | Berger |
| 2002/0095064 A1 | 7/2002 | Beyar |
| 2002/0095163 A1 | 7/2002 | Beyar et al. |
| 2002/0095181 A1 | 7/2002 | Beyar |
| 2002/0107525 A1 | 8/2002 | Harari et al. |
| 2002/0128681 A1 | 9/2002 | Broome et al. |
| 2002/0147382 A1 | 10/2002 | Neisz et al. |
| 2002/0151909 A1 | 10/2002 | Gellman et al. |
| 2002/0156487 A1 | 10/2002 | Gellman et al. |
| 2002/0156488 A1 | 10/2002 | Gellman et al. |
| 2002/0161382 A1 | 10/2002 | Neisz |
| 2002/0188169 A1 | 12/2002 | Kammerer et al. |
| 2003/0004395 A1 | 1/2003 | Therin |
| 2003/0009181 A1 | 1/2003 | Gellman et al. |
| 2003/0023136 A1 | 1/2003 | Raz |
| 2003/0023138 A1 | 1/2003 | Luscombe |
| 2003/0036676 A1 | 2/2003 | Scetbon |
| 2003/0045774 A1 | 3/2003 | Staskin et al. |
| 2003/0050530 A1 | 3/2003 | Neisz et al. |
| 2003/0065402 A1 | 4/2003 | Anderson et al. |
| 2003/0176875 A1 | 9/2003 | Anderson |
| 2004/0015057 A1 | 1/2004 | Rocheleau et al. |
| 2004/0039453 A1 | 2/2004 | Anderson et al. |
| 2004/0193215 A1 | 9/2004 | Harari et al. |
| 2004/0225181 A1 | 11/2004 | Chu et al. |
| 2004/0267088 A1 | 12/2004 | Krammerer |
| 2005/0000523 A1 | 1/2005 | Beraud |
| 2005/0004576 A1 | 1/2005 | Benderev |
| 2005/0131391 A1 | 6/2005 | Chu et al. |
| 2005/0131393 A1 | 6/2005 | Chu et al. |
| 2005/0199249 A1 | 9/2005 | Karram |
| 2005/0245787 A1 | 11/2005 | Cox et al. |
| 2005/0256530 A1 | 11/2005 | Petros |
| 2005/0277806 A1 | 12/2005 | Cristalli |
| 2005/0278037 A1 | 12/2005 | Delorme et al. |
| 2005/0283189 A1 | 12/2005 | Rosenblatt et al. |
| 2006/0058578 A1 | 3/2006 | Browning |
| 2006/0089524 A1 | 4/2006 | Chu |
| 2006/0089525 A1 | 4/2006 | Mamo et al. |
| 2006/0195007 A1 | 8/2006 | Anderson |
| 2006/0217589 A1 | 9/2006 | Wan et al. |
| 2006/0229493 A1 | 10/2006 | Weiser et al. |
| 2006/0229596 A1 | 10/2006 | Weiser et al. |
| 2006/0252980 A1 | 11/2006 | Arnal et al. |
| 2006/0260618 A1 | 11/2006 | Hodroff et al. |
| 2006/0287571 A1 | 12/2006 | Gozzi |
| 2007/0015953 A1 | 1/2007 | MacLean |
| 2007/0078295 A1 | 4/2007 | Landgrebe |
| 2007/0173864 A1 | 7/2007 | Chu |
| 2008/0039678 A1 | 2/2008 | Montpetit et al. |
| 2008/0300607 A1 | 12/2008 | Meade et al. |
| 2009/0012353 A1 | 1/2009 | Beyer |
| 2009/0182190 A1 | 7/2009 | Dann |
| 2009/0221867 A1 | 9/2009 | Ogdahl et al. |
| 2009/0221868 A1 | 9/2009 | Evans |
| 2010/0010631 A1 | 1/2010 | Otte et al. |
| 2010/0094079 A1 | 4/2010 | Inman et al. |

FOREIGN PATENT DOCUMENTS

| | | |
|---|---|---|
| DE | 2305815 | 2/1973 |
| DE | 10211360 | 9/2003 |
| DE | 20016866 | 3/2007 |
| EP | 4220283 C2 | 5/1994 |
| EP | 0650703 A1 | 6/1994 |
| EP | 0643945 A2 | 7/1994 |
| EP | 0632999 A1 | 1/1995 |
| EP | 1093758 A1 | 4/2001 |
| EP | 1342450 B1 | 9/2003 |
| FR | 2852813 A1 | 1/2004 |
| FR | 285217 | 10/2004 |
| GB | 2268690 A | 1/1994 |
| GB | 2353220 A | 10/2000 |
| SU | 1225547 A1 | 4/1986 |
| SU | 1342486 A | 10/1987 |
| WO | WO9310715 A1 | 6/1993 |
| WO | WO9319678 A2 | 10/1993 |
| WO | WO9511631 A1 | 5/1995 |
| WO | WO9525469 A1 | 9/1995 |
| WO | WO9716121 A1 | 5/1997 |
| WO | WO9730638 A1 | 8/1997 |
| WO | WO9747244 A1 | 12/1997 |
| WO | WO9819606 A1 | 5/1998 |
| WO | WO9835606 A1 | 8/1998 |
| WO | WO9835616 A1 | 8/1998 |
| WO | WO9842261 A1 | 10/1998 |
| WO | WO9853746 A1 | 12/1998 |
| WO | WO9937216 A1 | 7/1999 |
| WO | WO9937217 A1 | 7/1999 |
| WO | WO9952450 A1 | 10/1999 |
| WO | WO9953844 A1 | 10/1999 |
| WO | WO9958074 A2 | 11/1999 |
| WO | WO9959477 A1 | 11/1999 |
| WO | WO0013601 A1 | 3/2000 |
| WO | WO0030556 A1 | 6/2000 |

(56) References Cited

FOREIGN PATENT DOCUMENTS

| | | |
|---|---|---|
| WO | WO0040158 A2 | 7/2000 |
| WO | WO0057796 A1 | 12/2000 |
| WO | WO0074594 A1 | 12/2000 |
| WO | WO0074613 A1 | 12/2000 |
| WO | WO0074633 A2 | 12/2000 |
| WO | WO0232284 A2 | 4/2002 |
| WO | WO02030293 A1 | 4/2002 |
| WO | WO0234124 A2 | 5/2002 |
| WO | WO0239890 A2 | 5/2002 |
| WO | WO02058563 A1 | 8/2002 |
| WO | WO02062237 A1 | 8/2002 |
| WO | WO02069781 | 9/2002 |
| WO | WO02071953 A2 | 9/2002 |
| WO | WO03013392 A2 | 2/2003 |
| WO | WO03017848 A1 | 3/2003 |
| WO | WO03034939 A1 | 5/2003 |
| WO | WO03047435 A1 | 6/2003 |
| WO | WO03068107 A1 | 8/2003 |
| WO | WO03075792 A1 | 9/2003 |
| WO | WO03086205 A2 | 10/2003 |
| WO | WO03092546 A2 | 11/2003 |
| WO | WO03096928 A1 | 11/2003 |
| WO | WO03096929 A1 | 11/2003 |
| WO | WO2004016196 A2 | 2/2004 |
| WO | WO2004034912 A1 | 4/2004 |
| WO | WO2005004727 A1 | 1/2005 |
| WO | WO2005046511 A2 | 5/2005 |
| WO | WO2005048850 A2 | 6/2005 |
| WO | WO2005079702 A1 | 9/2005 |
| WO | WO2005122954 A1 | 12/2005 |
| WO | WO2006007189 A1 | 1/2006 |
| WO | WO2006007190 A1 | 1/2006 |
| WO | WO2006031879 A1 | 3/2006 |
| WO | WO2006069078 | 6/2006 |
| WO | WO2006108145 A1 | 10/2006 |
| WO | WO2007002012 A1 | 1/2007 |
| WO | WO2007002071 A1 | 1/2007 |
| WO | WO2007014241 A1 | 2/2007 |
| WO | WO2007016083 A1 | 2/2007 |
| WO | WO2007027592 A2 | 3/2007 |
| WO | WO2007059199 A2 | 5/2007 |
| WO | WO2007097994 | 8/2007 |
| WO | WO2007137226 A2 | 11/2007 |
| WO | WO2007146784 A2 | 12/2007 |
| WO | WO2007149348 A2 | 12/2007 |
| WO | WO2008057261 A2 | 5/2008 |
| WO | WO2008124056 A1 | 10/2008 |
| WO | WO2009005714 A2 | 1/2009 |
| WO | WO2009017680 A2 | 2/2009 |

OTHER PUBLICATIONS

Advantage A/T™, Surgical Mesh Sling Kit, Boston Scientific, 6 pages (2002).
Benderev, Theodore V., MD, A Modified Percutaneous Outpatient Bladder Neck Suspension System, Journal of Urology, vol. 152, pp. 2316-2320 (Dec. 1994).
Benderev, Theodore V., MD, Anchor Fixation and Other Modifications of Endoscopic Bladder Neck Suspension, Urology, vol. 40, No. 5, pp. 409-418 (Nov. 1992).
Capio™ CL—Transvaginal Suture Capturing Device—Transvaginal Suture Fixation to Cooper's Ligament for Sling Procedures, Boston Scientific, Microvasive®, 8 pages, (2002).
Cook/Ob Gyn®, Urogynecology, Copyright Cook Urological Inc., pp. 1-36 (1996).
Dargent, D. et al., Insertion of a Suburethral Sling Through the Obturator Membrane in the Treatment of Female Urinary Incontinence, Gynecol Obstet Fertil, vol. 30, pp. 576-582 (2002).
Gynecare TVT Tension-Free Support for Incontinence, The tension-free solution to female Incontinence, Gynecare Worldwide, 6 pages, (2002).
IVS Tunneller—A Universal instrument for anterior and posterior intra-vaginal tape placement, Tyco Healthcare, 4 pages (Aug. 2002).
IVS Tunneller—ein universelles Instrument fur die Intra Vaginal Schlingenplastik, Tyco Healthcare, 4 pages (2001).
Karram, Mickey M. et al., Chapter 19 Surgical Treatment of Vaginal Vault Prolapse, Urogynecology and Reconstructive Pelvic Surgery, (Walters & Karram eds.) pp. 235-256 (Mosby 1999).
Kovac, S. Robert, et al, Pubic Bone Suburethral Stabilization Sling: A Long Term Cure for SUI?, Contemporary OB/GYN, 10 pages (Feb. 1998).
SABRE™ Bioabsorbable Sling, Generation Now, Mentor, 4 pages (May 2002).
SABRE™ Surgical Procedure, Mentor, 6 pages (Aug. 2002).
Sanz, Luis E. et al., Modification of Abdominal Sacrocolpopexy Using a Suture Anchor System, The Journal of Reproductive Medicine, vol. 48, n. 7, pp. 496-500 (Jul. 2003).
Ulmsten, U. et al., An Ambulatory Surgical Procedure Under Local Anesthesia for Treatment of Female Urinary Incontinence, International Urogynecology Journal, vol. 7, pp. 81-86 (May 1996).
Ulmsten, Ulf et al., A Three Year Follow Up of Tension Free Vaginal Tape for Surgical Treatment of Female Stress Urinary Incontinence, British Journal of Obstetrics and Gynaecology, vol. 106, pp. 345-350 (1999).
Vesica® Percutaneous Bladder Neck Stabilization Kit, A New Approach to Bladder Neck Suspenison, Microvasive® Boston Scientific Corporation, 4 pages (1995).
Precision Twist, Low Profile design for Precise Anchor Placement, Boston Scientific Microvasive, 2001 2 pp.
Vesica Sling Kit, Microvasive Boston Scientific, 1997, 6pp.
Precision Tack, The Precise Approach to Transvaginal Sling Procedures, Boston Scientific, 1998, 4pp.

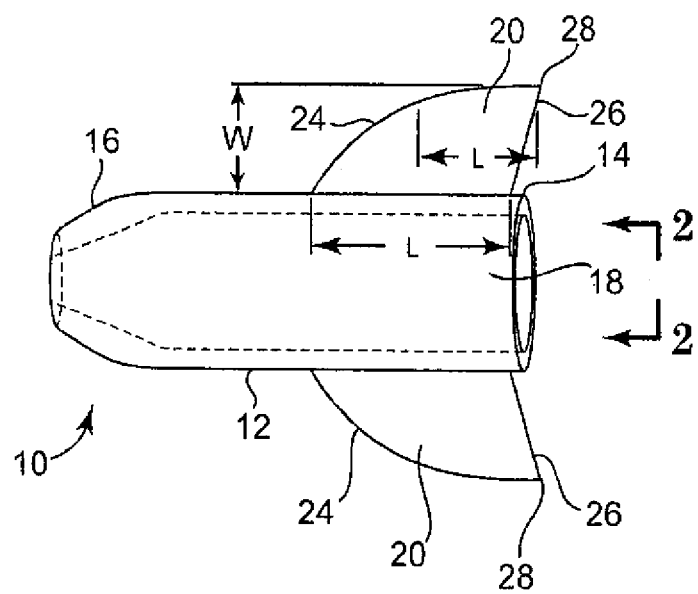
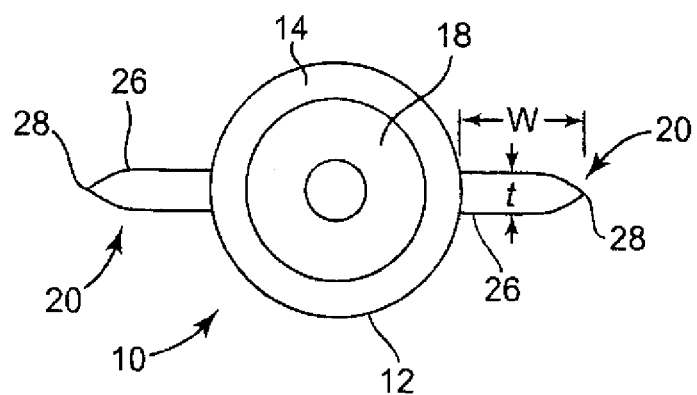

SURGICAL ARTICLES AND METHODS FOR TREATING PELVIC

PRIORITY CLAIM

This application is a continuation application of U.S. patent application Ser. No. 12/446,492, filed Oct. 27, 2010, which claims benefit from International Application No. PCT/US2007/022675, which was filed on Oct. 26, 2007, which in turn claims priority to U.S. Provisional Application Ser. No. 60/863,064, filed Oct. 26, 2006, by Jimenez et al., entitled "SINGLE INCISION SLING"; and U.S. Provisional Application Ser. No. 60/934,051, filed Jun. 11, 2007, by Dandah et al., entitled "SINGLE INCISION SLING," which applications are incorporated herein by reference in their entireties.

FIELD OF THE INVENTION

The invention relates to apparatus and methods for treating pelvic conditions by use of a pelvic implant to support pelvic tissue. The pelvic conditions include conditions of the female or male anatomy, and specifically include treatments of female or male urinary and fecal incontinence, treatment of female vaginal prolapse conditions including enterocele, rectocele, cystocele, vault prolapse, treatments of conditions of the pelvic floor, and any of these conditions in combination. In particular, the present invention relates to a surgically implanted implants that support pelvic tissue and that are secured to pelvic tissue to provide that support.

BACKGROUND

Pelvic health for men and women is a medical area of increasing importance, at least in part due to an aging population. Examples of common pelvic ailments include incontinence (fecal and urinary), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times.

Urinary incontinence can be characterized by the loss or diminution in the ability to maintain the urethral sphincter closed as the bladder fills with urine. Male or female stress urinary incontinence (SUI) occurs when the patient is physically stressed.

A specific area of pelvic health is trauma of the pelvic floor, e.g., of the levator ("levator ani") or coccygeus muscle (collectively the pelvic floor). The pelvic floor is made up of the levator and coccygeus muscles, and the levator is made up of components that include the puborectalis muscle, the pubococcygeus muscle, and the iliococcygeous muscle. For various reasons, the levator may suffer weakness or injury such as damage to the levator hiatus, ballooning or levator avulsion, any of which that can result in symptoms such as prolapse, fecal incontinence, and other conditions of the pelvis.

Levator defects (weakness or injury) can affect any portion of the levator, and can be especially common in the pubic portion of the levator ani, including the pubococcygeus and puborectalis muscles. Such defects are relatively common, for instance, in women with vaginal prolapse. Defects can also be present at the iliococcygeus muscle. Still other defects are in the form of a paravaginal defect, such as avulsion of the inferiomedial aspects of the levator ani from the pelvic sidewall; avulsion can refer to tissue being detached from the pubic bone, and may precede prolapse conditions. Another levator defect is levator ballooning, which refers to distension of levator muscles.

A different levator defect is a defect of the levator hiatus, which can reduce the stability of the pelvic floor and may result in sexual dysfunction, defecatory dysfunction, rectal prolapse, and fecal incontinence. Levator hiatus is also believed to play a significant role in the progression of prolapse. Embodiments of methods of the invention can address any of the conditions, as well as related conditions and symptoms.

SUMMARY

The present patent application describes pelvic implants, insertion tools, guides, and related methods for treating pelvic conditions such as incontinence (various forms such as fecal incontinence, stress urinary incontinence, urge incontinence, mixed incontinence, etc.), vaginal prolapse (including various forms such as enterocele, cystocele, rectocele, vault prolapse, etc.), and conditions of the pelvic floor. Embodiments of implants include a self-fixating tip, e.g., at a distal end of one or more extension portions. The self-fixating tip can be placed at and secured within internal tissue of the pelvic region to support an extension portion of the implant, and pelvic tissue that is supported by the implant. As an example, a self-fixating tip can be placed at tissue of the obturator foramen (this phrase referring to tissue that lies within or spans the obturator foramen, for example the obturator internus muscle, the obturator membrane, or the obturator externus muscle). Other tissue of the pelvic region can also be locations useful for implanting a self-fixating tip. According to specific embodiments of implants, a self-fixating tips can be designed to engage a distal end of an insertion tool to allow the insertion tool to place the self-fixating tip at a desired tissue location by pushing.

An implant can be implanted at the pelvic region by use of an insertion tool. Embodiments of insertion tools for use as described herein can include a needle tip that includes an aperture that allows for passage of guide. The aperture allows a user to use the guide to move the needle tip into engagement with a self-fixating tip (which is also engaged with the same guide), after the self-fixating tip has been placed at tissue of a patient's pelvic region. The aperture can also preferably allow the needle tip to engage the self-fixating tip while the needle tip is in engagement with the guide. This allows the needle tip to engage the self-fixating tip, located at tissue of a patient's pelvic region, and allow the self-fixating tip to be adjusted after initial placement at tissue of a pelvic region.

Alternately or in addition to an aperture at a needle tip, certain embodiments of needle tips for use according to the present description can include one or more extension guard at the distal end of the needle at a location where the distal end meets a self-fixating tip. An extension guard is a portion of an insertion tool that extends laterally from a needle and is shaped to correspond to a shape or form of a trailing (proximal) portion of a self-fixating tip when the self-fixating tip is engaged with the needle tip. The extension guard provides streamlining behind (proximal to) a trailing surface of a self-fixating tip, such as behind a base or a lateral extension of a self-fixating tip. The streamlining can reduce the force required to remove a self-fixating tip from tissue or to adjust the location of the self-fixating tip in a direction opposite of the direction of insertion. The combined form of a needle extension guard situated proximal to a trailing surface of a lateral extension or other trailing surface of a self-fixating tip includes a smooth, e.g., streamlined, form from a proximal end to a distal end.

Methods of the invention can include a step of initially placing a self-fixating tip at a location at tissue of the pelvic region, followed by adjusting the placement if desired. The initial placement may first be performed, and the placement may be tested to determine if adjustment is necessary. If so, the needle tip may be re-engaged with the self-fixating tip previously placed at the tissue, e.g., by guiding an aperture at the needle tip along a guide that extends to a proximal side of the self-fixating tip. The guide leads the needle tip to the self-fixating tip, and the needle can be re-engaged with the self-fixating tip. The insertion tool can then be used to push the self-fixating tip to a location of deeper penetration into the tissue In one aspect, the invention relates to an insertion tool that includes a handle and a needle extending from the handle. The needle includes a proximal end attached to the handle and a distal end that includes a needle tip. The needle tip includes an aperture that allows guided relative movement of the needle tip along a guide.

In another aspect, the invention relates to a method of preparing an assembly for surgical treatment. The method includes: providing an insertion tool that includes a needle that includes a needle tip having an aperture, and an implant having a self-fixating tip; providing a guide engaged with the self-fixating tip; engaging the self-fixating tip with the needle tip in a configuration that allows the needle to push the self-fixating tip; and passing the guide through the aperture in the needle tip.

Yet another aspect of the invention relates to a method of treating a pelvic condition. The method includes providing a combination, including an insertion tool that includes a needle that includes a needle tip having an aperture, and an implant having a self-fixating tip; engaging the self-fixating tip with the needle tip in a configuration that allows the needle to push the self-fixating tip; inserting the needle tip and self-fixating tip through an incision in a patient into a pelvic region; and using the needle to insert the self-fixating tip into tissue of the pelvic region.

Another aspect of the invention relates to a method of treating a pelvic condition. The method includes providing an implant comprising a tissue support portion, an extension portion, and a self-fixating tip at an end of the extension portion, the self-fixating tip comprising a lateral extension; and providing an insertion tool comprising a handle and a needle extending from the handle, the needle comprising a proximal end attached to the handle and a distal end that includes a needle tip. The insertion tool includes an extension guard at the distal end that, when the needle tip engages the self-fixating tip to allow the needle to push the self-fixating tip for surgical installation, the extension guard is located proximal to the lateral extension and reduces the force required to move the self-fixating tip in a proximal direction through muscle tissue. The method further includes: engaging the self-fixating tip with the needle tip in a configuration that allows the needle to push the self-fixating tip, inserting the needle tip and self-fixating tip through an incision in a patient into a pelvic region, using the needle to insert the self-fixating tip into tissue of the pelvic region and without removing the needle from the self-fixating tip, using the needle to increase or decrease the amount of penetration of the self-fixating tip into the pelvic tissue.

According to yet another aspect of the invention, the invention relates to a method of treating a pelvic condition by providing a combination including a sling and an insertion tool. The insertion tool includes a needle tip that has an aperture for engaging a guide. The sling is a urethral sling that includes two self-fixating tips each including: a base having a proximal base end and a distal base end, the proximal base end being connected to one of the extension portions; and two fixed lateral extensions extending from the base. The method includes: creating a single medial incision in a male or female anatomy; dissecting toward tissue to be supported; contacting a tissue support portion of the implant with tissue to be supported; implanting a self-fixating tip at an obturator foramen on one side of the patient by using the needle to cause the self-fixating tip to penetrate tissue of the obturator foramen; and implanting a second self-fixating tip at an obturator foramen on an opposing side of the patient by using the needle to cause the self-fixating tip to penetrate tissue of the obturator foramen. Further according to the method, the first self-fixating tip, the second self-fixating tip, or both, is implanted by: providing a guide; passing the guide through an aperture of the self-fixating tip; using the needle to cause the self-fixating tip to penetrate tissue of the pelvic region and removing the needle from the self-fixating tip; leaving an end of the guide external to the incision; passing the guide through the aperture in the needle tip; and guiding the aperture along the guide and engaging the needle tip with the self-fixating tip previously inserted in the tissue.

In another aspect, the invention relates to a combination that includes a pelvic implant and insertion tool. The implant includes a support portion, an extension portion, and a self-fixating tip connected to the extension portion. The self-fixating tip includes a base that has a proximal base end and a distal base end, the proximal base end being connected to the extension portion; and a lateral extension extending from the base. The insertion tool includes a handle and a needle extending from the handle. The needle includes: a proximal end attached to the handle and a distal end that includes a needle tip configured to engage the self-fixating tip. The insertion tool includes an extension guard that, when the needle tip engages the self-fixating tip to allow the needle to push the self-fixating tip for surgical installation, the extension guard is located proximal to the lateral extension and reduces the force required to move the self-fixating tip in a proximal direction through muscle tissue.

BRIEF DESCRIPTION OF DRAWINGS

FIG. 1 illustrates as side view of an embodiment of a self-fixating tip.

FIG. 2 illustrates an end view of an embodiment of a self-fixating tip.

Figure 3A:
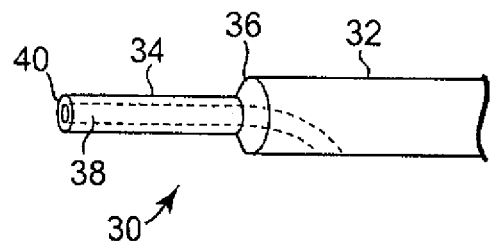
FIGS. 3A, 3B, 3C, 3D, and 3E illustrate side views of various embodiments of needle tips.

All figures are schematic and not necessarily to scale.

DETAILED DESCRIPTION

The invention relates to surgical instruments, assemblies, combinations (e.g., of implants and tools), and implantable articles for treating pelvic floor disorders such as prolapse (e.g., vaginal prolapse), incontinence (urinary and fecal incontinence), conditions of the pelvic floor such as the perineal body, conditions of levator muscle (such as a component of levator muscle), conditions of the levator hiatus, and combinations of two or more of these. According to various embodiments, a surgical implant can be used to treat a pelvic condition, wherein the method includes placing an implant in a manner to support tissue of the pelvic region in a male or female. Methods involve the use of an implant and insertion tool, the implant including at least one self-fixating tip that becomes implanted into tissue of the pelvic region.

Certain embodiments of implants and tools can be designed and used according to the current description in a manner that allows for placement and adjustment of a self-fixating tip. The adjusting methods may be by using an insertion tool to insert the self-fixating tip to place the self-fixating tip at an initial position, checking the position of the self-fixating tip or implant to identify whether adjustment is necessary or desired, and then using the insertion tool again to move the self-fixating tip to a deeper position within tissue, or, alternately, to move the self-fixating tip to a position of less tissue penetration relative to a position of initial placement.

Certain embodiments of a tool and self-fixating tip can be designed for use in conjunction with a guide that facilitates re-engaging the needle tip and self-fixating tip previously implanted at tissue. The insertion tool includes a needle, and the needle includes an aperture at the needle tip that is capable of engaging the guide. The guide can be used in conjunction with the aperture to allow a user to lead the needle tip to the self-fixating tip of the implant, and engage (or re-engage) the self-fixating tip, after the self-fixating tip has been initially placed in tissue of the pelvic region. Upon engagement (or re-engagement), the position of the self-fixating tip can be adjusted as desired, by further insertion into the tissue.

According to embodiments of the invention that involve a guide and a needle tip having an aperture, the tool may be dis-engaged from the self-fixating tip, and the position of the self-fixating tip or implant can then be checked to identify whether adjustment is necessary or desired. If adjustment is necessary or desired, the guide can be used to re-engage the needle tip with the self-fixating tip implanted at pelvic tissue.

Upon the needle tip being re-engaged with the self-fixating tip, the needle may be used to cause the self-fixating tip to be pushed to a deeper position within tissue.

Additionally or alternately to a guide and needle tip aperture, in certain embodiments of methods and tools, to allow for adjustment of the position of a self-fixating tip, the self-fixating tip can include a lateral extension and the tool can be designed to include an extension guard. The extension guard becomes positioned proximal to the lateral extension to reduce the amount of force required to move the self-fixating tip in a direction opposite of the direction of insertion.

According to such embodiments, the engagement of the tool and the self-fixating tip may be not disturbed (i.e., the tool can remain engaged with the self-fixating tip implanted at pelvic tissue) while the position of the self-fixating tip or implant is checked to identify whether adjustment is necessary or desired. If adjustment is necessary or desired, the insertion tool can be used to move the self-fixating tip to a deeper position within tissue, or, alternately, to a position of less tissue penetration. In these embodiments, a guide may not be required to assist in re-engaging the needle tip with the self-fixating that has been implanted in the pelvic tissue.

An implant can include a tissue support portion (or "support portion") that can be used to support pelvic tissue such as the bladder or urethra (which includes any location of the bladder, urethra, bladder neck, mid-urethra, or proximal end of the urethra), vaginal tissue, tissue of the perineum, coccygeus, levator ani, levator hiatus, rectum, etc., as discussed herein. During use, the tissue support portion is typically placed in contact with and optionally attached to tissue to be supported, such as with a suture, biological adhesive, mechanical attachment, or any other mode of attachment. An implant can additionally include one or more extension portion (otherwise known as "end" portions or "arms") attached to the tissue support portion. Examples of pelvic implants are described in the following exemplary documents: U.S. Pat. No. 7,070,556; United States patent publication numbers 2005/0245787; 2006/0195011; 2006/0195010; 2006/0235262; 2006/0287571; 2006/0195007; 2006/0260618; 2006/0122457; 2005/0250977; and International patent application number PCT/US2006/028828, having an International Filing Date of Jul. 25, 2006; International patent application, number PCT/US2007/016760, having an International Filing Date of Jul. 25, 2007; International patent application number PCT/US2007/014120, having an International Filing Date of Jun. 15, 2007; and International patent publication WO 2007/097994, the entireties of each of these disclosures being incorporated herein by reference.

An implant may include portions or sections that are synthetic or of biological material (e.g., porcine, cadaveric, etc.). Extension portions may be, e.g., a synthetic mesh such as a polypropylene mesh. The tissue support portion may be synthetic (e.g., a polypropylene mesh) or biologic. Examples of implant products that may be similar to those useful according to the present description, include those sold commercially by American Medical Systems, Inc., of Minnetonka Minn., under the trade names Apogee® and Perigee® for use in treating pelvic prolapse (including vaginal vault prolapse, cystocele, enterocele, etc.), and Sparc®, Bioarc®, and Monarc® for treating urinary incontinence.

Exemplary implants can include a tissue support portion for placing in contact with tissue to be supported and one or more "extension" portion, the tissue support portion being useful to support a specific type of pelvic tissue such as the urethra, bladder (including the bladder neck), vaginal tissue (anterior, posterior, apical, etc.), perineum, rectum, levator ani, coccygeus, tissue of the pelvic floor, or other tissue of the pelvic region. The tissue support portion can be sized and shaped to contact the desired tissue when installed, e.g., as a "sling" or "hammock," to contact and support pelvic tissue. A tissue support portion that is located between two or more extension portions is sometimes referred to herein as a "central support portion" or a "support portion."

Extension portions are elongate pieces of material that extend from the tissue support portion and either are or can be connected to the tissue support portion, and are useful to attach to an anatomical feature of the pelvic region (e.g., using a self-fixating tip) to thereby provide support for the tissue support portion and the supported tissue. One or multiple (e.g.; one, two, or four) extension portions can extend from the tissue support portion as elongate "ends," "arms," or "extensions," useful to attach to tissue in the pelvic region.

An example of a particular type of pelvic implant is the type that includes supportive portions including or consisting of a central support portion and either two, four, or six elongate extension portions extending from the central support portion. An implant that has exactly two extension portions can be of the type useful for treating, e.g., urinary incontinence, anterior vaginal prolapse, or posterior vaginal prolapse. An implant having four or six extension portions can be useful for treating combinations of these conditions. The term "supportive portions" refers to extension portions and tissue support portions and does not include optional or appurtenant features of an implant or implant system such as a sheath, self-fixating tip or other type of connector for attaching the implant to an insertion tool, guide, etc.

Examples of implants for treating incontinence, e.g., urethral slings, can include a central support portion and two extension portions, and may take the form of an integral mesh strip. An exemplary urethral sling can be an integral mesh strip with supportive portions consisting of or consisting essentially of a central support portion and two extension portions. Examples of urethral slings for treating male urinary incontinence can have a widened central support portion, as discussed, for example, in Assignee's copending United States patent publication numbers 2006/0287571 and 2006/0235262. Other exemplary urethral sling implants are described in Assignee's U.S. Pat. No. 7,070,556; United States publication numbers 2006/0195010 and 2006/0195007; and International application numbers WO 2007/097994 and WO 2007/014120; among others.

Examples of implants for treating vaginal prolapse can comprise a central support portion and from two to four to six extension portions, and may take the form of an integral piece of mesh or multiple pieces of mesh attached in a modular fashion. See, e.g., Assignee's copending United States patent publication numbers 2006/0260618; 2005/0245787; 2006/0122457; 2005/0250977; and International patent application number PCT/2006/028828; among others.

Examples of implants for treating conditions of the pelvic floor, such as to support tissue of the perineal body, to treat levator avulsion, to treat levator ballooning, to support or repair levator ani muscle, to tighten or reduce the size of levator hiatus, to treat vaginal prolapse, or to treat fecal incontinence, may take the form of an integral piece of mesh or multiple pieces of mesh attached in a modular fashion. See, e.g., International patent application number PCT/US2007/016760, filed Jul. 25, 2007, by Kimberly Anderson, entitled SURGICAL ARTICLES AND METHODS FOR TREATING PELVIC CONDITIONS.

Dimensions of an implant can be as desired and useful for any particular installation procedure, treatment, patient anatomy, and to support or repair a specific tissue or type of tissue. Exemplary dimensions can be sufficient to allow the tissue support portion to contact tissue to be repaired or supported, and to allow extension portions to extend from the tissue support portion to a desired anatomical location to allow the extension portion be secured to anatomy of the pelvic region, to support the tissue support portion.

Dimensions of extension portions according to the invention can allow an extension portion to reach between a tissue support portion placed to support pelvic tissue (at an end of the extension portion connected to the tissue support portion) and a location at which the distal end of the extension portion attaches to pelvic tissue. A distal end of an extension portion can include a self-fixating tip that can be attached directly to pelvic tissue such as pelvic muscle, ligament, or tendon. The length of the extension portion, therefore, can be in a range that allows placement of a tissue support portion as desired to support pelvic tissue, while the self-fixating tip is placed in pelvic tissue.

A length of an extension portion can optionally be fixed (i.e., the extension portion does not include any form of length-adjusting mechanism), as can a length of an implant spanning from opposite self-fixating tips and including extension portions and a length or segment of tissue support portion. Alternate implants may include adjustment or tensioning mechanisms that allow a physician to alter the length of an extension portion before, during, or after implantation: e.g., International application number PCT/US2007/014120, filed Jun. 15, 2007, by Dockendorf et al., titled SURGICAL IMPLANTS, TOOLS, AND METHODS FOR TREATING PELVIC CONDITIONS.

Alternately, adjustment and tensioning mechanisms can also be excluded from embodiments of implants of the invention by selecting the length of extension portions and tissue support portions, and by adjusting for tensioning or positioning of extension portions and tissue support portions based on placement of the self-fixating tip within the pelvic tissue, selected placement including selection of the point of insertion of a self-fixating tip and depth of insertion of the self-fixating tip, and by use of adjustment steps described herein that include options of initial placement of a self-fixating tip followed by adjustment to place the self-fixating tip either deeper or less deep into tissue relative to the initial placement position.

An extension portion of an implant can include a self-fixating tip at an end of the extension portion that is distal from a tissue support portion. The self-fixating tip in general can be a structure connected to a distal end of an extension portion and that can be implanted into tissue in a manner that will maintain the position of the self-fixating tip and the attached implant. Optionally, a self-fixating tip can also be designed to engage a distal end of an insertion tool so the insertion tool can be used to push the self-fixating tip into tissue for implantation, then optionally adjust the placement. The self-fixating tip may engage the insertion tool at an internal channel of the self-fixating tip, at an external location such as at the base, or at a lateral extension, as desired.

A self-fixating tip can be made out of any useful material, generally including materials that can be molded or formed to a desired structure and connected to or attached to an end of an extension portion of an implant. Useful materials can include plastics such as polyethylene, polypropylene, and other thermoplastic or thermoformable materials, as well as metals, ceramics, and other types of biocompatible and optionally bioabsorbable or bioresorbable materials. Exemplary bioabsorbable materials include, e.g., polyglycolic acid (PGA), polylactide (PLA), copolymers of PGA and PLA, and the like.

A self-fixating tip also, preferably, includes one or more lateral extension that can increase the force required to remove the self-fixating tip from tissue after insertion into the tissue, i.e. the "pullout force." At the same time, a lateral extension can be designed to exhibit a reduced or relatively low "insertion force," which is the amount of force used to insert the self-fixating tip into tissue. Embodiments of self-fixating tips can be designed to be essentially permanently placed upon insertion into tissue, except that according to methods described herein, a self-fixating tip can be initially placed then adjusted as described.

Factors that can be balanced in designing a self-fixating tip as described include insertion force and pullout force, the insertion force being preferably reduced or minimized while a pullout force allows removal of the self-fixating tip only when desired by a surgeon during an implantation procedure. Concurrently, the self-fixating tip design can attempt to minimize the amount of potential trauma caused to tissue by inserting or, when necessary, removing, a self-fixating tip. A desired combination of these factors can be achieved by selecting size, shape, and other structural features of the self-fixating tip and the elements of the self-fixating tip such as a base and lateral extensions.

Another factor that can balance the above performance properties of a self-fixating tip can be the number of lateral extensions. A self-fixating tip can have from one to any desired number of lateral extensions, but it has been found that a self-fixating tip can function well with a small number of fixed lateral extensions such as two, three, or four lateral extensions. To provide desired dimensions of a self-fixating tip, such as reduced overall length, embodiments of self-fixating tips can include two or more lateral extensions located at the same position along the longitudinal dimension (length) of the base between a proximal base end and a distal base end. A self-fixating tip that includes exactly two lateral extensions, for example, can include two self-fixating tips that are located opposite of each other along a length of a base, to provide desired insertion and pullout forces, especially by implanting the two lateral extensions to be oriented in fibrous tissue with the direction of the lateral extensions being not parallel to the tissue fibers, for example being perpendicular to the fibers (or "across the grain"). Also, a relatively low number of lateral extensions, such as two, can desirably reduce the amount of trauma when, as may become necessary at the discretion of a surgeon during implantation, a self-fixating tip must be adjusted or withdrawn from tissue after placement.

Other feature of a self-fixating tip for use according to the present description can be sizes of a base, lateral extension, or both, to allow the self-fixating tip to be inserted into tissue at a selected depth. As an example, a lateral extension that will be placed into muscle tissue can have a length dimension (measured along a longitudinal axis of the base) that allows the self-fixating tip to be inserted into the tissue at any selected depth along the thickness of the tissue. This can mean that the length dimension of the lateral extension is shorter than the total depth of tissue (e.g., muscle or other tissue) into which the self-fixating tip will be placed.

A base of a self-fixating tip can be of any desired size, shape, and dimension (e.g., length, diameter, width). A diameter of a cylindrical base can be any useful size, for example from about 2 to about 5 millimeters. The diameter may be uniform along the length of the base, between a base proximal end and a base distal end, or a diameter may be non-uniform. For example, a diameter of a base may be greater at a proximal end and taper to a reduced diameter at a distal end, to optionally reduce insertion force or increase pullout force.

The diameter or diameter profile of a base may preferably be relatively small, e.g., minimized, to reduce trauma to tissue when implanted or removed. The diameter can also be sufficient to allow placement of a desired number of lateral extensions around the perimeter of the base.

Exemplary self-fixating tips described herein include a cylindrical base or tapered cylindrical base, with a hollow or solid interior. Other shapes for a base may also be useful, such as blocks having square or rectangular forms when viewed in cross section along a longitudinal axis extending from a proximal base end to a distal base end. For those types of self-fixating tips, dimensions of a square or rectangular cross section can be of a range similar to the described range of diameters of a cylindrical base, such as from about 2 to about 5 millimeters in either dimension when viewed in cross section.

As examples of specific ranges of lengths of exemplary self-fixating tips, lengths (measured from the proximal base end to the distal base end along a longitudinal axis of the self-fixating tip) in the range from 0.4 to 1.0 centimeter, e.g., from 0.4 to 0.8 centimeters, or from 0.4 to 0.7 centimeters, have been found to be useful. These ranges are specifically useful for self-fixating tips that can be inserted into tissue of the obturator internus, because the relatively short length can allow the self-fixating tip to be inserted into the muscle tissue a desired depth, i.e., over a range of depths, optionally without penetrating the obturator membrane. More generally, the self-fixating tip can be of a length dimension that is less than the thickness of muscle or other pelvic tissue into which the self-fixating tip is to be inserted, so the self-fixating tip can be inserted a desired distance into the tissue.

According to exemplary embodiments, a self-fixating tip can have structure that includes a base having a proximal base end and a distal base end. The proximal base end can be connected (directly or indirectly, such as by a connective suture) to a distal end of an extension portion of an implant. The base extends from the proximal base end to the distal base end and can optionally include an internal channel extending from the proximal base end at least partially along a length of the base toward the distal base end. The optional internal channel can be designed to interact with (i.e., engage) a distal end of an insertion tool (e.g., a needle tip) to allow the insertion tool to be used to place the self-fixating tip at a location within pelvic tissue of the patient. Optionally, the channel can be an aperture that extends through the entire length of the base to allow a guide to be loosely engage by the self-fixating tip.

Alternate embodiments of self-fixating tips do not require and can exclude an internal channel for engaging an insertion tool. These alternate embodiments may be solid, with no internal channel, and may engage an insertion tool, if desired, by any alternate form of engagement, such as by use of an insertion tool that contacts the self-fixating tip at an external location, for example by grasping or otherwise contacting the base (on a side or at the face of the proximal base end) or by grasping or otherwise contacting a lateral extension.

Exemplary lateral extensions can be rigid or "fixed" relative to the base so the lateral extension does not substantially move or deflect during or after implantation. For example, a fixed lateral extension can be a lateral extension that is not substantially moveable relative to the base in a manner that certain types of known soft tissue anchor extensions are moveable, for instance between a non-deployed or non-extended position that places an extension against the base to allow insertion of the anchor into tissue with a reduced size or shape profile, and a deployed or extended position that places the extension away from the base to engage tissue and prevent movement of the self-fixating tip in a direction opposite of the direction of insertion. Alternate embodiments of lateral extensions can be moveable or deflectable, if desired, such as to allow a reduced insertion force by use of lateral extensions that deflect backward (toward the proximal base end or against the base) when a self-fixating tip is being pushed through tissue.

A lateral extension can have a three-dimensional form that results in a balance of the performance factors described herein, including insertion force, pullout force, and reduced trauma caused to tissue during insertion or in the event of a need to adjust or remove the self-fixating tip during an implantation procedure. A lateral extension can include a three-dimensional form referred to as an extension body defined as the lateral extension material between a leading edge, a trailing edge, and a boundary at which the lateral extension connects to a base. Away from the boundary of the lateral extension and the base, the far lateral edge of a lateral extension may include a point of connection of the trailing edge and the leading edge; alternately, another segment or connection may connect the leading edge with the trailing edge away from their respective connections to the base.

The "leading edge" means the boundary of the lateral extension on the side of the lateral extension toward the base distal end, which is also the edge that leads the lateral extension body and contacts tissue first as the self-fixating tip is being inserted into tissue by pushing. The "trailing edge" means the boundary of the lateral extension on the side of the lateral extension toward the base proximal end, which is also the edge that trails behind the lateral extension body and passes through or contacts tissue last when the self-fixating tip is being inserted into tissue by pushing.

The lateral extension body can exhibit a thickness or thickness profile as desired, such as a uniform thickness or a varied thickness across the extended area of the lateral extension body. For example, embodiments of implants may include a leading edge of a low profile, e.g., reduced thickness or even sharpened, to allow for reduced insertion force. According to these embodiments, the thickness of the lateral extension body can reduce gradually or taper from a central portion of the body (away from edges) in the direction of a leading edge. A leading edge, being of a reduced thickness to reduce insertion force, may optionally in addition exhibit a form that extends in a direction back toward the trailing edge, i.e., a "swept-back" leading edge, to reduce insertion force. The shape of a leading edge may be linear or arcuate, and if arcuate may be convex or concave. Optionally a leading edge may take an arcuate convex path that sweeps back to meet the trailing edge at a single lateral extension point away from the base. E.g., see the exemplary self-fixating tip illustrated at FIG. 1.

The direction and shape of a trailing edge of a lateral extension, as the edge extends away from the base (e.g., when viewed as in FIG. 1), may be linear or arcuate, and if arcuate may be convex or concave relative to the lateral extension body. A trailing edge can be as desired, such as arcuate, straight, convex, flat, linear, rounded, tapered, sharp, blunt, etc. Optionally a trailing edge can exhibit a thickness (a thickness dimension, t, is illustrated, e.g., at FIG. 2) to produce increased pullout force.

Viewing the trailing edge along the longitudinal axis of the base and looking at the proximal base end (as in FIG. 2), a trailing edge can exhibit an area that includes a width (W, the distance the trailing edge extends laterally away from the base) and a thickness (t, the distance perpendicular to the width and the longitudinal axis of the self-fixating tip). An exemplary width of a trailing edge can be, e.g., in the range from 0.5 to 3 millimeters.

An exemplary thickness at a trailing edge may be the same as a thickness at an interior or central portion of the lateral extension (away from the leading and trailing edges), or a thickness at a trailing edge may be a maximum thickness of the entire lateral extension, meaning for example that the thickness increases from a narrow thickness at the leading edge and widens gradually to a maximum thickness at the trailing edge. A thickness of a trailing edge can be, e.g., in the range from 0.2 to 2 millimeters, e.g., from 0.5 to 1.5 millimeters.

Based on the above-described exemplary thickness and width dimensions, a surface area of a trailing edge may be, e.g., from the range from 0.25 to 5 square millimeters, e.g., from 0.5 to 4, or from 1 to 3 square millimeters. The surface area of the trailing edge may be concave, convex, rounded, tapered (symmetrically or toward one or the other surfaces of the lateral extension), etc.

A lateral extension can also include a third dimension that can be referred to as a "length" dimension (shown as "L" at FIG. 1). A length can be measured at a location where the lateral extension meets or extends from the base. This length dimension can become smaller as the lateral extension extends away from the base. An exemplary length of a lateral extension at the location of the lateral extension meeting the base can be, e.g., from 0.5 to 5 millimeters, such as from 1 to 4 millimeters or from 1.5 to 3.5 millimeters.

In the specific example of a self-fixating tip for insertion into tissue of the obturator foramen, an exemplary length of a lateral extension can be a length that is less than the total thickness of obturator foramen tissue (i.e., the combined thickness of obturator internus muscle, obturator, membrane, and obturator externus muscle); a length of a lateral extension intended to be inserted into the obturator internus muscle can be a length that is a portion of the thickness of the obturator internus muscle, e.g., less than 1 centimeter, such as less than 0.5 centimeter.

As noted, a self-fixating tip can include multiple lateral extensions at multiple locations, either at different positions along a length of a base, at different locations around a perimeter of a base, or both. With self-fixating tips of reduced dimensions (to achieve functionality as described), a self-fixating tip may preferably include all lateral extensions originating from the same position along a length of a base, e.g., a single set of lateral extensions can be arranged around a perimeter of a base, each extending in a different direction but from the same portion of length between the proximal base end and the distal base end.

A self-fixating tip can be connected to an extension portion of an implant in any fashion, directly by any attachment mechanism, or indirectly such as through an attachment structure such as a suture. A connection can be based on a mechanical structure, by adhesive, by a connecting suture, or by an integral connection such as by injection molding or "insert" molding (also, "overmolding") as described U.S. Publication No. 2006/0260618-A1, incorporated herein by reference. According to that description a thermoplastic or thermosetting polymer material can be insert molded or injection molded at an end of a mesh extension portion of an implant, e.g., directly to the mesh. By this method, a molded polymer can form a self-fixating tip at an end of an extension portion. The self-fixating tip can be as described herein, for example, including lateral extensions and an internal channel.

A single example of a self-fixating tip, for purposes of non-limiting illustration and explanation, is at FIG. 1. FIG. 1 shows self-fixating tip 10, including base 12 (for attachment to an implant extension end), proximal base end 14, distal base end 16, internal channel 18, and two lateral extensions 20 located on outer surfaces and on opposite sides of base 12. Self-fixating tip 10 can be prepared from a biocompatible material, preferably a biocompatible material such as a biocompatible polymer, which may optionally be bioresorbable or bioabsorbable. Exemplary self-fixating tip 10 as illustrated includes internal channel 18 (optional according to the invention) which is an opening within base 12 extending from proximal end 14 toward distal end 16 along at least a portion of the total longitudinal length of base 12. Internal channel 18 is capable of receiving a distal end (e.g., needle tip) of an elongate needle of an insertion tool to allow self-fixating tip 10 to be pushed into position within pelvic tissue during an implant installation procedure. Channel 18, optionally and as illustrated can be an "aperture" or "bore" that extends entirely through base 12, from proximal base end 14 to distal base 16, allowing a guide to be threaded loosely within channel 18.

Lateral extensions 20 include leading edge 24 and trailing edge 26. Leading edge 24 originates at base 12 and extends away from base 12 along an arcuate pathway sweeping back toward proximal base end 14, meeting trailing edge 26 at point 28. Leading edge 24 can preferably include a reduced thickness or a sharp or sharpened edge. Trailing edge 26 is shown to be relatively straight but could alternately be arcuate, concave, or convex (from the direction viewed in FIG. 1). Trailing edge 26 has a flat surface area (not visible at FIG. 1), but could also be arcuate, concave, or convex. Trailing edge 26 is shown to sweep slightly back in a proximal direction, although it could alternately extend straight away from (i.e. perpendicular to) base 12 or extend away from base 12 in a direction that includes a forward component, i.e., a directional component in the direction of distal base end 16.

Referring now to FIG. 2, self-fixating tip 10 is viewed in a direction looking at proximal base end (surface) 14 along a longitudinal axis of base 12. In this view, surface areas of lateral extensions 20 are shown as flat surfaces of approximately the area of thickness (t) by width (W). Not shown in FIG. 2 is an optional feature of a surface area within self-fixating tip 10 that fixes the rotational position of the self-fixating tip relative to a longitudinal axis of a needle tip of an insertion tool, such as a flat surface, a key, etc. A surface to fix the rotational position of the self-fixating tip relative to a longitudinal axis of the needle tip can be particularly useful in embodiments of the invention that include a needle having extension guards.

Embodiments of self-fixating tips may engage a guide. A "guide" refers to an elongate element that can also engage an aperture of a needle tip. A guide may be a thread, suture, plastic or metal wire, or the like, that includes at least one end that can be loose to extend from a self-fixating implanted in pelvic tissue to a location external to a patient's body, during a procedure for installing the self-fixating tip, and that optionally includes two loose ends that can both at the same time extend from a self-fixating tip to a location external to a patient's body during a procedure for installing the self-fixating tip. The guide may be of any useful dimensions. An exemplary length may be from 10 to 60 centimeters, e.g., from 20 to 50 centimeters. An exemplary diameter may be from 0.1 to 2 millimeter, e.g., from 0.2 to 1 millimeter. A single example of a guide can be 2-0 suture material.

A self-fixating tip being "engaged with" a guide refers to an association between a self-fixating tip and a guide, during use, wherein the guide engages the self-fixating tip in a fixed manner such as a permanent attachment, or a loose manner such as a manner by which the guide can support the self-fixating tip as the self-fixating tip is moveable along a length of the guide. As one example, a self-fixating tip engaged with a guide refers to a self-fixating tip that is securely attached to a guide in a fixed manner such as by being tied to the self-fixating tip, embedded within the self-fixating tip (e.g., by molding the self-fixating tip around a guide), or adhered by any type of mechanical fastener or adhesive (see, for example, FIGS. 6 and 8). A self-fixating tip engaged with a guide also refers to a self-fixating tip that is loosely engaged through an aperture of a self-fixating tip (see, for example, FIGS. 5A, 5B, and 7). A self-fixating tip engaged with a guide, still further, refers to a self-fixating tip that loosely engages a guide such as through an aperture, and that can become more securely fixed relative to the self-fixating tip at least on one direction; for example a guide may be contained by an aperture of a self-fixating tip and may include a structure such as a knot or other structure that is larger in diameter compared to a diameter of the aperture so that the structure (e.g., knot) is capable of contacting the self-fixating tip to become fixed at a location of the self-fixating tip in a manner that allows the guide to encounter resistance within the self-fixating tip. The knot or other structure can become lodged at the aperture to allow the guide to place force on the self-fixating tip and to pull the self-fixating tip (see, for example, FIG. 9).

An insertion tool can be used to install the implant. Various types of insertion tools are known and these types of tools and modified versions of these tools can be used according to the present description, to install an implant as described. Examples of useful tools include those types of tools that generally includes a thin elongate needle that attaches to a handle; a handle attached to one end (a proximal end) of the needle; and a distal end of the needle adapted to engage a self-fixating tip in a manner that allows the needle to push the self-fixating through a tissue path and insert the self-fixating tip into tissue of the pelvic region. This class of tool can be used with a self-fixating tip that includes an internal channel designed to be engaged by a distal end of an insertion tool. Other general types of insertion tools will also be useful by engaging a self-fixating tip in a manner that does not involve an internal channel of a self-fixating tip. These alternate insertion tools may for example contact or grasp a proximal base end of a self-fixating tip in the absence of an internal channel, such as by grasping an external surface of the base. An alternate insertion tool may contact or grasp a side of the base, a lateral extension, or any other portion of the self-fixating tip or base, in a way that allows the insertion tool to engage the self-fixating tip and insert the self-fixating tip at a desired location within tissue of the pelvic region.

Exemplary insertion tools for treatment of pelvic conditions are described, e.g., in U.S. Pat. No. 7,070,556; United States patent publication numbers 2005/0245787, 2006/0235262, 2006/0260618, and 2005/0250977; and International patent application numbers PCT/US2006/028828 and PCT/2007/016760, among others. The tools of the above-referenced patent documents may be curved in two or three dimensions and may include, for example, a curved portion for placing an extension portion of an implant through a tissue path that passes from a region of the urethra to tissue of an obturator foramen, or another pelvic tissue location.

Exemplary insertion tools for use according to the invention can be similar to or can include features of tools described in the above-referenced patent documents. For use according to methods described herein, those insertion tools may be modified to allow the insertion tool to be used to place a self-fixating tip at tissue within the pelvic region by methods described herein, including initial placement of a self-fixating tip followed by optional adjustment of the self-fixating tip.

The insertion tool can be designed, shaped, and sized, to include an elongate inserter or "needle" that may be straight or that may be curved in two or three dimensions, that can be inserted through an incision that provides access to the pelvic region. The incision may be, for example, a vaginal incision (for female anatomy), a perineal incision (for male anatomy), or an incision in the rectal or buttock region, inner thigh or groin, pubic region, etc.

Some previous insertion tools are designed to reach through a vaginal or perineal incision, through an internal tissue path, and to then extend through a second external incision, e.g., at the inner groin, thigh, abdominal area, or perirectal region. Alternate insertion tools also useful with embodiments of the presently-described methods can be sized and shaped to place a self-fixating tip at an internal location of the pelvic region without the need to be sufficiently long to extend from a vaginal or perirectal incision to another (e.g., external) incision. The length can be only sufficient to reach from a vaginal or perirectal incision to an obturator foramen, for example, or to any other location within the pelvic region at which a self-fixating tip is desirably placed. The length may be sufficient, for example, to reach from a vaginal or perirectal incision to a different muscle or tissue, such as a levator ani, coccygeous muscle, iliococcygeous muscle, arcus tendineus, sacrospinous ligament, etc., to place a self-fixating tip at one of those tissues.

In general, a tool according to the present discussion can include a handle, needle (including a shaft), needle tip, and needle tip end. The handle is at the portion of the tool that will be referred to as a proximal end, and the needle tip is at a distal end. A proximal end of the needle connects to a distal end of the handle. The "needle tip" refers to a length of a needle that is at the far distal end, including a needle tip end, which is the most distal location of the needle. The needle tip includes a portion of the needle that (if included) is designed to engage a self-fixating tip, and also may be considered to include a small amount of length (e.g., 1 centimeter or 2 centimeters) of the needle shaft adjacent to the surfaces designed to engage a self-fixating tip.

Some embodiments of tools for use as described herein can include a needle tip that includes an aperture that allows the needle tip to engage a guide. Generally, an "aperture" is a feature at a needle tip that can engage a guide to allow the needle to move in a guided fashion along a length of the guide. This, for example, allows a user to use the guide to move the needle tip into engagement with a self-fixating tip (which is also engaged with the same guide), after the self-fixating tip has been placed at tissue of a pelvic region. Also, preferably, the aperture is designed to allow the needle tip to engage the self-fixating tip while the needle tip is engaged with the guide. This allows the needle tip to engage the self-fixating tip, located at tissue of a patient's pelvic region, and allow the self-fixating tip to be adjusted after initial placement at tissue of a pelvic region.

An aperture at a needle tip can include a circular or cylindrical bore, or a functional equivalent, that can be, e.g., along a longitudinal axis of the needle tip, parallel to a longitudinal axis of the needle tip, diagonal relative to a longitudinal axis of the needle tip but through the axis, diagonal relative to a longitudinal axis of the needle tip and also either through or not through the axis, etc. A bore may be cylindrical, but may also be square, rectangular, or any other geometry. An aperture may be substantially linear or curved along a length extending along a length of the needle tip or needle shaft. An embodiment of a bore portion of an aperture may extend from a needle tip end or any other surface of a needle tip, in a direction along the needle toward the proximal end of the needle. An aperture can include a bore that connects to a slot or a channel at a surface of the needle tip, within which the guide may be loosely contained.

An aperture may be arcuate, e.g., cylindrical, or partially cylindrical in cross section, with a dimension that can engage a guide, e.g., may include a diameter in the range from 0.10 to 2 millimeters, preferably from 0.5 to 1.5 millimeters. A length dimension of an aperture (include a bore, channel, or both) can be, e.g., in the range from 0.1 millimeter, to a length of a needle shaft or an insertion tool, including a handle, (e.g., if a shaft or tool is fully cannulated). Alternate length dimensions can be sufficient for an aperture to extend along a portion of a length of a needle tip.

An example of a needle tip that includes an aperture is illustrated at FIG. 3A. As shown, needle tip 30 includes needle shaft 32, narrowed portion 34, and shoulder 36 that connects shaft 32 with narrowed portion 34. Narrowed portion 34 is designed to engage a channel that extends within a base of a self-fixating tip (not shown). Aperture 38 is a continuous cylindrical bore that extends from needle tip end 40, through narrowed portion 34, and through a portion of needle shaft 32, including a curved portion that allows aperture 34 to exit at a surface of needle shaft 32. Aperture 38 extending from needle tip end 40 to needle shaft 32 is capable of engaging a guide, which can be threaded through the aperture. In use, the guide can be threaded through the aperture and the needle tip can be led along the guide to a desired location of anatomy of a patient; the guide can at the same time be engaged with a self-fixating tip that has been placed at pelvic tissue of a patient. The needle tip can then engage the self-fixating tip previously placed within the tissue, allowing the insertion tool to be used to adjust the location of the self-fixating tip.

Figure 3B:
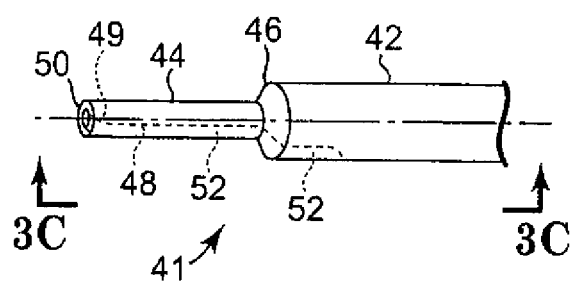

Another embodiment of a needle tip that includes an aperture is shown at FIG. 3B. As shown, needle tip 41 includes needle shaft 42, narrowed portion 44, and shoulder 46 that connects shaft 42 with narrowed portion 44. Narrowed portion 44 is designed to engage a channel within a base of a self-fixating tip (not shown). Aperture 48 includes a cylindrical bore, 49, that begins at needle tip end 50 and extends generally along a longitudinal axis (or slightly diagonally to the axis) of needle tip 50 into narrowed portion 44. Moving proximally into narrowed portion 44, aperture 48 includes open channel (or "slot" or "recess") 52 within which a guide can fit, such as when needle tip 41 engages a self-fixating tip. Channel 52 extends along a surface of narrowed portion 44, along shoulder 46, and along a distance of shaft 42. Aperture 48, extending from needle tip end 50 to needle shaft 52, is capable of engaging a guide, which can be threaded through bore 49 and contained by aperture 48 while needle tip 50 engages a self-fixating tip. In use, the guide can be threaded through bore 49 and the needle tip can be led along the guide to a desired location of anatomy of a patient; the guide can at the same time be engaged with the self-fixating tip previously placed at the location of anatomy. The needle tip can then engage a self-fixating tip previously placed within tissue at that location, while the guide is contained by aperture 48, and the insertion tool can be used to adjust the location of the self-fixating tip.

Figure 3C:
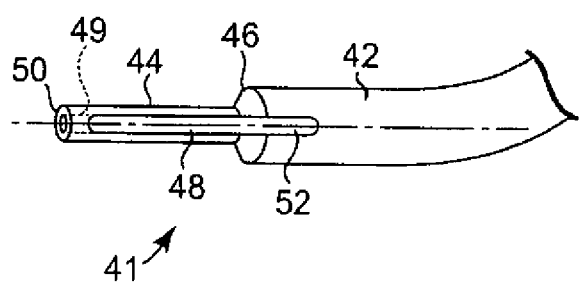

FIG. 3C illustrates a rotated view of needle tip 41 shown at FIG. 3B. This view again shows aperture 48, including cylindrical bore 49 that begins at needle tip end 50 and extends generally along a longitudinal axis of needle tip 50, into narrowed portion 44. Open channel (or "slot" or "recess") 52 is shown directly as being defined by a recessed surface extending along narrowed portion 44, within which a guide can fit. Channel 52 extends along a surface of narrowed, portion 44, along shoulder 46, and along a distance of shaft 42.

Figure 3D:
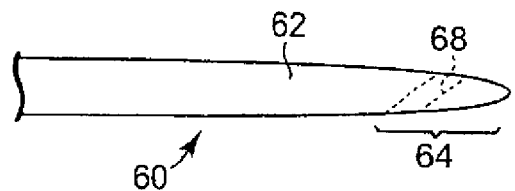

Another example of a needle tip that includes an aperture is illustrated at FIG. 3D. As shown, needle tip 60 includes needle shaft 62, tapered portion 64, and aperture 68. Tapered portion 34 can be designed to engage an opening within a base of a self-fixating tip (not shown), or may be designed for insertion into tissue in a manner that allows a guide to be pulled through aperture 68; with needle tip 60 placed in tissue of the pelvic region, a loose end of the guide can be pulled to cause a self-fixating tip to be pulled into the tissue. Aperture 68 is a continuous cylindrical bore that extends from a surface at tapered portion 64, in a direction that is diagonal, proximally toward shaft 62, exiting at shaft 62 at or near the proximal side of tapered portion 64.

Figure 3E:
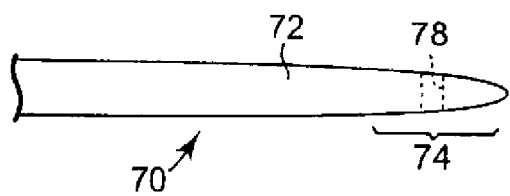

Another example of a needle tip that includes an aperture is illustrated at FIG. 3E. As shown, needle tip 70 includes needle shaft 72, tapered portion 74, and aperture 78. Tapered portion 74 can be designed to engage an opening within a base of a self-fixating tip (not shown), or may be designed for insertion into tissue in a manner that allows a guide to be pulled through aperture 78; with needle tip 70 placed in tissue of the pelvic region, a loose end of the guide can be pulled to cause a self-fixating tip to be pulled into the tissue. Aperture 78 is a continuous cylindrical bore that extends transversely through tapered portion 74 of needle tip 72.

Figure 3F:
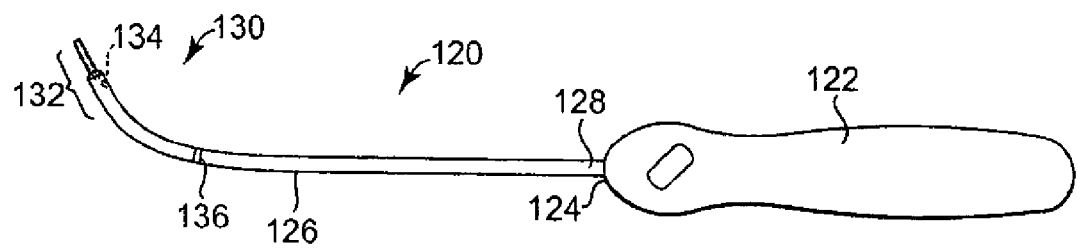
FIG. 3F illustrates an embodiment of an insertion tool.

FIG. 3F illustrates an insertion tool that includes a needle tip having an aperture. As illustrated, tool 120 includes handle 122 that includes handle distal end 124. Needle 126 includes proximal end 128 attached to handle distal end 124. Needle distal end 130 include needle tip 132 that includes aperture 134. Mark 136, which may be a groove or other marking, can function to mark a reference point at which the mark can be located when needle tip 132 is properly located to place a self-fixating tip at tissue of the pelvic region. For example, for placing a urethral sling in a male or female, mark 136 may indicate the midline of a patient, e.g., below the urethra, when the needle tip is placed for implanting a self-fixating tip at tissue of the pelvic region. This allows the surgeon or other user to avoid causing a self-fixating tip to be penetrated too deeply in desired tissue. A mark such as mark 136 may also be used to mark a reference point relative to a location of an implant, e.g., by corresponding to a midline or other location of an implant, to allow a surgeon or other user to assess the distance of the needle tip relative to that location; a mark on a insertion tool needle aligned with a location of the implant, for example, may indicate that the needle tip is engaged with a self-fixating tip at the end of an extension portion of the implant.

Alternately or in addition to an aperture at a needle tip as described, a needle tip of a tool for use according to the present description can include one or more extension guard at the distal end of the needle at a location where the distal end meets a self-fixating tip. An extension guard is an integral or attached portion of an insertion tool, located at the needle, that extends laterally from a needle shaft and that is shaped to correspond to a shape or form of a trailing (proximal) portion of a self-fixating tip when the self-fixating tip is engaged with the needle tip. An extension guard can be integral to a needle or may be a removable piece that can be fit onto the needle and removed as desired, such as a plastic attachment in the form of a tube, clip, or other moveable or attachable and detachable piece that fits the needle at a position along the length of the needle so the extension guards extend laterally.

The function of the extension guard is to provide streamlining behind (proximal to) a trailing surface of a self-fixating tip, such as behind a lateral extension of a self-fixating tip; the streamlining reduces the force required to remove a self-fixating tip from tissue or to adjust the location of the self-fixating tip in a direction opposite of the direction of insertion. The combined form of a needle extension guard situated proximal to a trailing surface of a lateral extension of a self-fixating tip includes a smooth, e.g., streamlined, form from a leading edge of the lateral extension to a proximal end (trailing edge) of the extension guard. The smooth form can be preferably arcuate and can exclude jagged edges or angles that would increase friction when the self-fixating tip is moved through tissue (e.g., pushed or pulled) while engaged with the needle tip. The streamlined form results in reduced friction, and reduced force, for moving the assembly of self-fixating tip and needle distal end in a direction of insertion, and particularly, in a direction opposite of a direction of insertion.

Figure 4A:
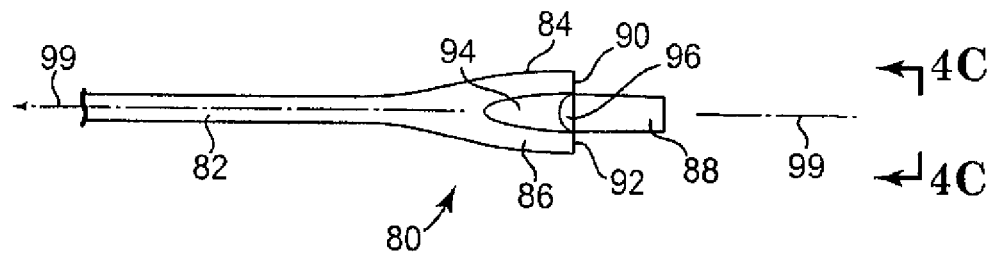
FIGS. 4A and 4B illustrate a side view and a perspective view of an embodiment of needle tip.

As an example of a needle tip that includes an extension guard, needle tip 80 is shown at FIG. 4A. As shown by this side view, needle tip 80 includes needle shaft 82, top extension guard 84, bottom extension guard 86, pin 88, and side extension guard 94. Top extension guard 84 includes top extension guard face 90. Bottom extension guard 86 includes bottom extension guard face 92. Side extension guard 94 includes side extension guard face 96. Each of extension guard faces 90, 92, and 96 can be independently sized to correspond to a size and shape of a trailing (i.e. proximal-facing) surface of a self-fixating tip, such a trailing surface of a lateral extension. An extension guard that "corresponds to" a trailing surface of a self-fixating tip, refers to a profile of an extension guard—when looking along a longitudinal axis of the tool—that is substantially the same as a profile of a trailing surface of the self-fixating tip. See, e.g., FIG. 4C and associated text. When the needle tip engages the self-fixating tip, the distal surfaces of the extension guards correspond in size and shape to the trailing (proximal) surfaces of the self-fixating tip.

Still referring to FIG. 4A, pin 88 is designed to engage an internal channel of a self-fixating tip. While needle tip 80 as illustrated does not include an aperture, as described herein, an aperture as described could be included in needle tip 80.

Figure 4B:
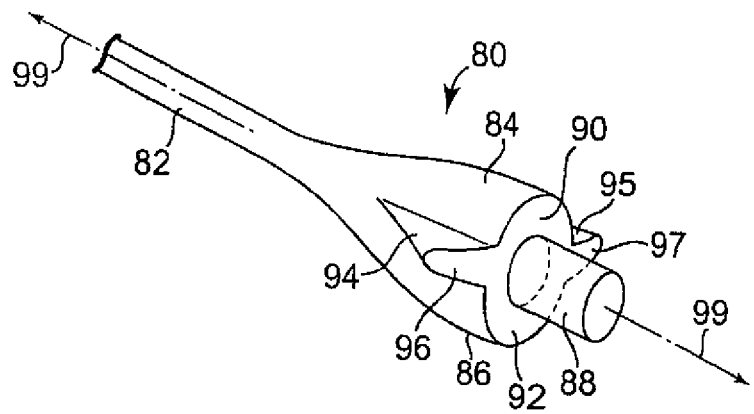
Figure 4C:
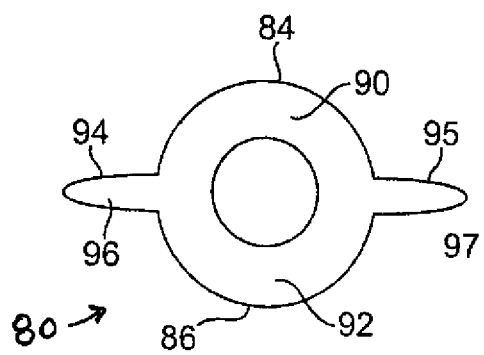
FIG. 4C illustrates an end view of an embodiment of a needle tip.

FIG. 4B is a side profile view of needle tip 80. FIG. 4C is a front view of needle tip 80 along longitudinal axis 99 of needle tip 80. Not illustrated at FIGS. 4A, 4B, and 4C, is a feature of a needle tip 80, a surface that corresponds to a surface of a self-fixating tip, to cause the needle tip to engage the self-fixating tip at a rotational position so that side extension guards 94 and 95 are oriented proximal to extension portions of the self-fixating tip. Control of the rotational position of the self-fixating tip, when engaging the needle tip, can be particularly useful in embodiments of the invention that include a needle having extension guards, so the needle guards are aligned with the extension portions.

Figure 4D:
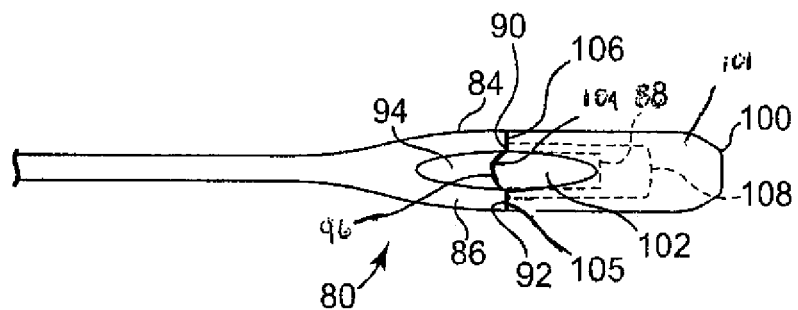
FIGS. 4D and 4E illustrate a side view and a tip view, respectively, of a needle tip engaged with a self-fixating tip.
Figure 4E:
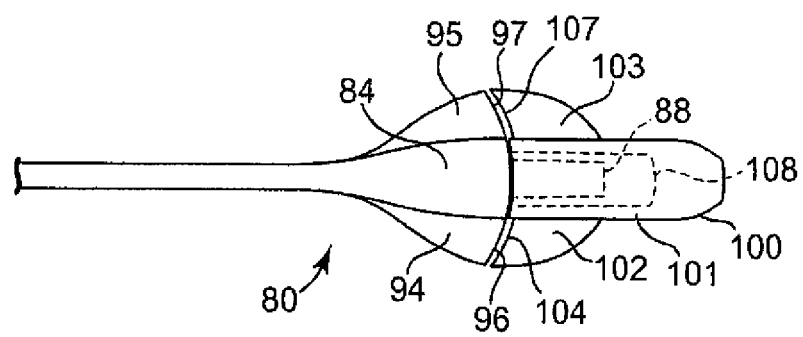

FIGS. 4D and 4E illustrate needle tip 80 engaged with self-fixating tip 100. Self-fixating tip 100 includes base 101, which includes internal channel 108 that is sized and shaped to engage pin 88. Lateral extensions 102 and 103 extend from base 101. Trailing surfaces (i.e., "trailing faces") of self-fixating tip 100 are sized and shaped to correspond to distal surfaces of extension guards at needle tip 80. As illustrated, trailing face 104 of lateral extension 102 corresponds with side extension guard face 96. Similarly, trailing face 105 of base 101 corresponds in size and shape with bottom extension guard face 92, and trailing face 106 of base 101 corresponds in size and shape with top extension guard face 90. As additionally shown at FIG. 4E, trailing face 107 of lateral extension 103 corresponds with side extension guard face 97 of extension guard 95. Preferably, channel 108 can include a surface that corresponds to a surface of pin 88 that together cause selective rotational engagement between pin 88 and self-fixating tip 100, to allow engagement only with alignment of distal surfaces 96 and 97 of side extension guards 94 and 95 of the insertion tool, with trailing surfaces 104 and 107 of lateral extensions 102 and 103 of the needle tip, respectively.

FIGS. 4A, 4B, 4C, etc., show extension guards as integral elements of a needle. An extension guard can be integral to a needle as illustrated, but optionally can be removable, such as in the form of a tube that fits over a length of the needle on a proximal side of the needle tip, with side extension guards extending laterally in a position where the side extension guards will be proximal to lateral extension of the self-fixating tip during use.

Generally, tools and implants as described are useful for treating conditions of the pelvic region, such as any one or more of incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), conditions of the perineal body, conditions of the pelvic floor including the coccygeous and levator muscle (such as by treating a component of levator muscle, iliococcygeous, coccygeous, levator ani, pubococcygeous), conditions of the levator hiatus, and combinations of two or more of these, and other pelvic conditions caused by muscle and ligament weakness.

By any method, an embodiment of an insertion tool can be used, as described, wherein the insertion tool can include a needle tip having an aperture capable of engaging a guide, an extension guard, or both. The extension guard can be removable, and a single insertion tool that includes an aperture and a removable extension guard can be used with or without the extension guard within a single surgical implantation procedure.

Certain embodiments of methods as described can include a step of engaging a self-fixating tip (of an implant) with a needle tip of an insertion tool, wherein the needle tip includes an aperture that is capable of engaging a guide, and the self-fixating tip also engages the guide. The insertion tool is used to initially place the self-fixating tip at a desired tissue location in the pelvic region. When placing the self-fixating tip, the guide includes one end or portion of a total length that is engaged with the self-fixating tip, and at least one portion (e.g., a proximal portion) that includes an end that remains accessible and outside of the surgical site, optionally two portions each including an end. The accessible (loose) portion, end, portions, or ends, can remain external to the incision.

According to these embodiments, after initial placement of a self-fixating tip at tissue of the pelvic region, placement of the self-fixating tip can be assessed to see if adjustment is desired, e.g., by checking tension of the extension portion visually, by feel (e.g., by application of pressure), or by checking patient comfort, continence, etc. If adjustment is desired, using a tool having a needle tip with an aperture, an end of the guide can be threaded through the aperture and the guide can be used to lead the needle tip to the self-fixating tip that has been initially placed in tissue. The tool can be used to push the self-fixating tip deeper into the tissue. The position can be checked again, and further adjustment can performed if desired. Such adjustment can be performed during the procedure, or afterward, e.g., hours or days later. The guide, may remain engaged with the self-fixating tip until final adjustment is performed, then optionally removed.

According to exemplary methods that use a tool that includes extension guards, a self-fixating tip can be adjusted by either increasing or reducing the degree of penetration of the self-fixating tip into the tissue. This tool can be used for initial placement of the self-fixating tip and can remain engaged with the self-fixating tip after the self-fixating tip has been initially placed. The extension guards will line up on the proximal side of surfaces (e.g., lateral extensions) of the self-fixating tip to reduce the amount of friction and trauma associated with moving the self-fixating tip in a direction opposite of the direction of insertion. The position can be checked without dis-engaging the needle tip from the implanted self-fixating tip. If adjustment of the position is desired, the insertion tool can be used to move the self-fixating tip either deeper or less deep into the tissue. The position can be checked again and further adjustment can performed if desired. This embodiment of the invention does not require a guide. However, a guide can be used if the option of still further adjustment may be desired after the needle tip has been dis-engaged from the self-fixating tip, in which case the further adjustment deeper into the tissue can be performed using an insertion tool that includes an aperture at the needle tip, as described elsewhere.

According to methods that include a guide and a needle tip that includes an aperture that can engage the guide, the needle tip aperture can be engaged with the guide at any useful stage in a surgical procedure. According to certain specific embodiments of the invention, an aperture of a needle tip may be engaged with a guide prior to initial placement of a self-fixating tip. After initial placement of the self-fixating tip, the needle tip can be dis-engaged from the self-fixating tip and the placement of the self-fixating tip can be assessed. If adjustment is desired the aperture of the needle tip can be engaged with the guide and the needle tip can be led along the guide to the self-fixating tip and the needle tip can be engaged with the self-fixating tip (previously placed in the tissue).

Certain embodiments of the described methods can be performed with an aperture (e.g., channel) of a self-fixating tip that loosely engages a guide, by threading the guide through the aperture in the self-fixating tip. A proximal guide portion having a proximal guide end can enter the self-fixating tip at the proximal end of the base, and a distal guide portion having a distal guide end can exit and extend from the distal end of the base. According to such exemplary embodiments, a distal guide portion or a proximal guide portion can be marked at a location of either end that remains external to the patient during an implantation procedure, to allow a surgeon to differentiate the two different guide portions. For example, a knot or other marking can be placed at either guide portion. Preferably, a mark such as a knot can be placed at the end of a distal guide portion so that the proximal (non-marked) guide portion can be identified as the guide portion with which an aperture of a needle tip can be engaged to allow the needle tip to be led to the proximal end of the base of the self-fixating tip. After placement of the self-fixating tip at desired tissue of the pelvic region, and optional adjustment, the insertion tool can be removed from (disengaged from) the self-fixating tip and removed from the patient. If no further adjustment is necessary the guide can be removed from the patient by pulling the distal guide portion so the proximal guide portion moves distally through the aperture of the implanted self-fixating tip and the entire guide disengages the self-fixating tip.

Figure 5A:
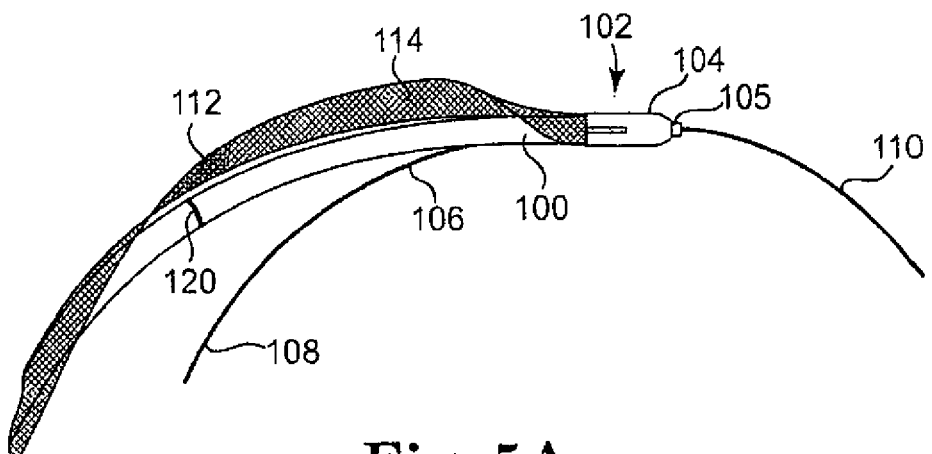
FIGS. 5A and 5B illustrate a side view and a bottom view, respectively, of a combination of an implant that includes a self-fixating tip, engaged with a needle tip, each also engaged with a guide.

Referring to FIGS. 5A (side view) and 5B (top view), illustrated is a combination of an insertion tool engaged with a self-fixating tip, and a guide loosely engaged with (i.e., threaded through) the self-fixating tip as well as an aperture at a needle tip of the insertion tool. Insertion tool needle 100 includes needle tip 102 (not specifically shown), which includes needle tip end 105. Needle tip 102 is engaged with self-fixating tip 104 through a central channel of self-fixating tip 104. The central channel extends completely through a base of self-fixating tip 104 as an aperture into which needle tip 102 extends. Needle tip end 105, as illustrated, extends beyond the length of self-fixating tip 104. Needle tip 102 includes an aperture (not specifically shown) within which guide 106 is loosely engaged, e.g., threaded. The needle tip aperture begins at needle tip end 105 and extends to a proximal location along the length of needle 100. Guide 106 includes proximal guide portion 108 and distal guide portion 110. Proximal guide portion 108 exits a proximal end of needle tip 102 and a proximal end of self-fixating tip 104, and can be used to lead a needle tip from an external location to the proximal end of self-fixating tip 104. Distal guide portion 110 exits a distal end of needle tip 102 and through an aperture at needle tip end 105. Optionally and not shown, distal guide portion 110 may be marked to distinguish from proximal guide portion 108, e.g., by tying a knot at distal guide portion 110.

Figure 5B:
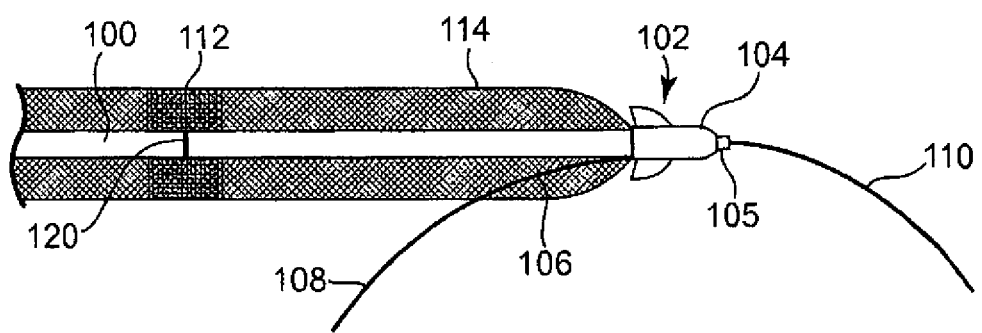

Also shown at FIGS. 5A and 5B is mesh 114, e.g., a portion of a urethral sling, that includes an extension portion connected to the proximal end of self-fixating tip 104, and a tissue support portion. Marking 112 indicates the median of the sling. Groove 120 is at a location of shaft 100 that corresponds to the median of the implant (when the needle tip is engaged with the self-fixating tip) and also to the location of the urethra when, in use during an implantation procedure, the needle tip is placed at a desired location for placement of a self-fixating tip, such as at an obturator foramen.

Figure 6:
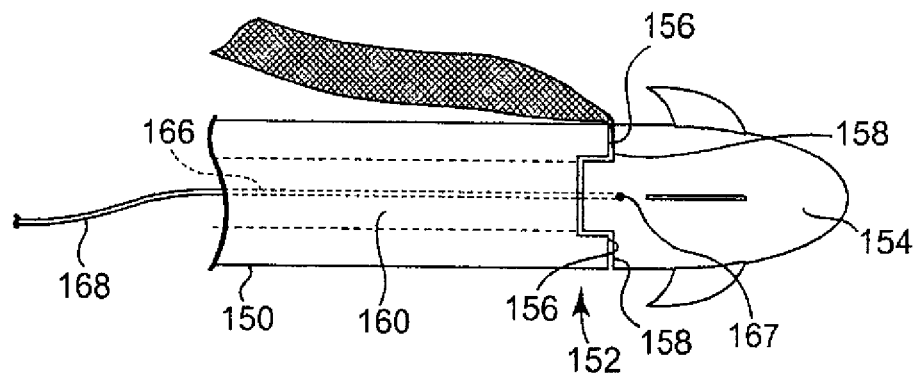
FIG. 6 illustrates an embodiment of a needle tip engaged with a self-fixating tip.

An alternate combination of insertion tool engaged with a self-fixating tip, and a guide engaged with the insertion tool and the self-fixating tip, is at FIG. 6. In this embodiment, a guide is not loosely engaged with the self-fixating tip but is engaged by being securely fixed to the self-fixating tip. Referring to FIG. 6, insertion tool needle 150 includes needle tip 152 engaged with self-fixating tip 154. Engagement surfaces 156 of needle tip 152 engage trailing surfaces 158 of self-fixating tip 154, in a manner that allows the insertion tool to push self-fixating tip 154 into tissue. Needle tip 152 includes aperture 160 within which guide 166 is loosely engaged, i.e., threaded. End 168 of guide 166 is securely fixed to self-fixating tip 154. Guide 166 includes proximal guide portion 168 and fixed guide end 167. Proximal guide portion 168 enters needle tip 152 through aperture 160 and can extend through a desired length of needle 150, e.g., to exit needle 150 at any desired location, such as at a distal end of needle 150, at a proximal end of needle 150, or at a handle attached to a proximal end of needle 150. Fixed guide end 167 is secured to self-fixating tip 154. Needle 150 is attached at a proximal end to a handle (not shown). Needle 150, the attached handle, or both, may be fully cannulated from needle tip 152 to a proximal end of needle 150 or proximal end of the tool, e.g., the handle, to allow proximal guide portion 168 to be available at a location external to the patient incision during an implantation procedure. Proximal guide portion 168 can be used to lead needle tip 152 to the proximal end of self-fixating tip 154, after self-fixating tip 154 has been initially placed at tissue of the pelvic region.

Figure 7:
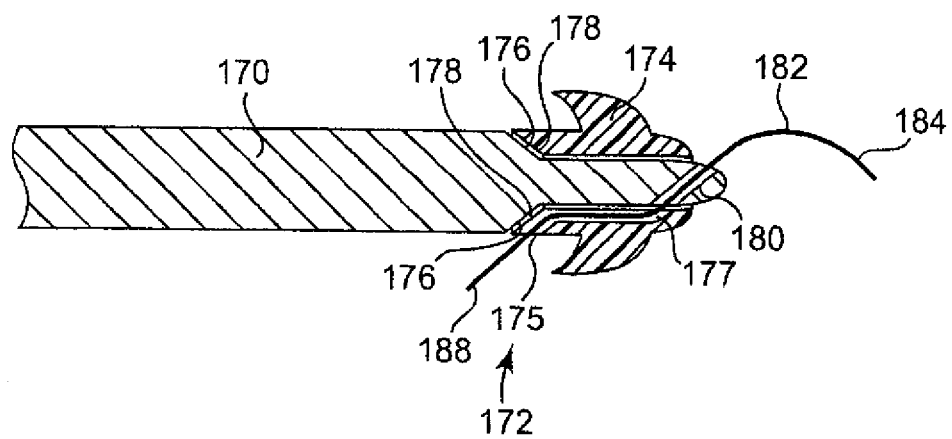
FIG. 7 illustrates an embodiment of a needle tip engaged with a self-fixating tip.

Yet another combination of insertion tool engaged with a self-fixating tip, and a guide engaged with the self-fixating tip, is at FIG. 7. In this embodiment, a guide is loosely engaged with the self-fixating tip, and is also loosely engages with the needle tip. In this embodiment the guide passes through an aperture or channel located along a length of the self-fixating tip, in addition to an aperture in the needle tip. Referring to FIG. 7, insertion tool needle 170 includes needle tip 172 engaged with self-fixating tip 174. Engagement surfaces 176 of needle tip 172 engage trailing surfaces 178 of self-fixating tip 174 in a manner that allows the insertion tool to push self-fixating tip 174 into tissue. Needle tip 172 includes aperture (bore) 180 within which guide 182 is loosely engaged, i.e., threaded. Guide 182 passes loosely through aperture 180, exits a distal end of aperture 180, and extends distally as distal guide portion 184. Guide 182 also includes proximal guide portion 188, which enters self-fixating tip 174 through aperture 175, extends through aperture (e.g., bore or channel) 177 of self-fixating tip 174, to enter aperture 180. Optionally and not shown, distal guide portion 184 may be marked to distinguish from proximal guide portion 188, e.g., by tying a knot at distal guide portion 184.

Figure 8A:
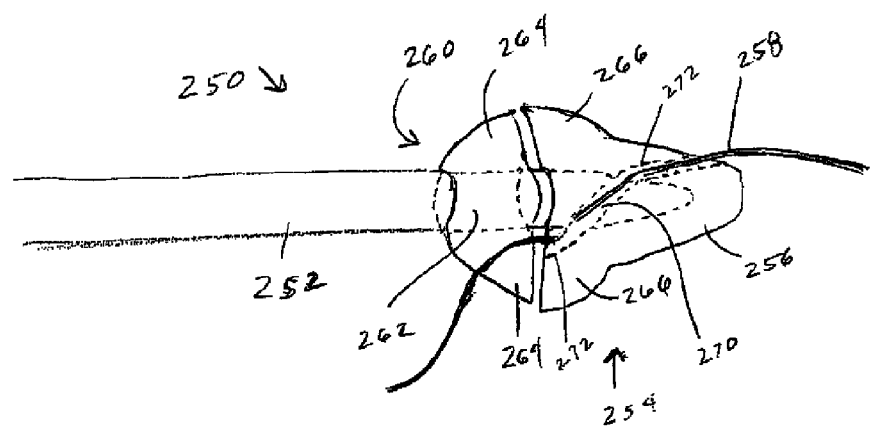
FIGS. 8A and 8B illustrate two different configurations of an embodiment of a needle tip engaged with a self-fixating tip, the needle tip and self-fixating tip also being engaged with a guide.
Figure 8B:
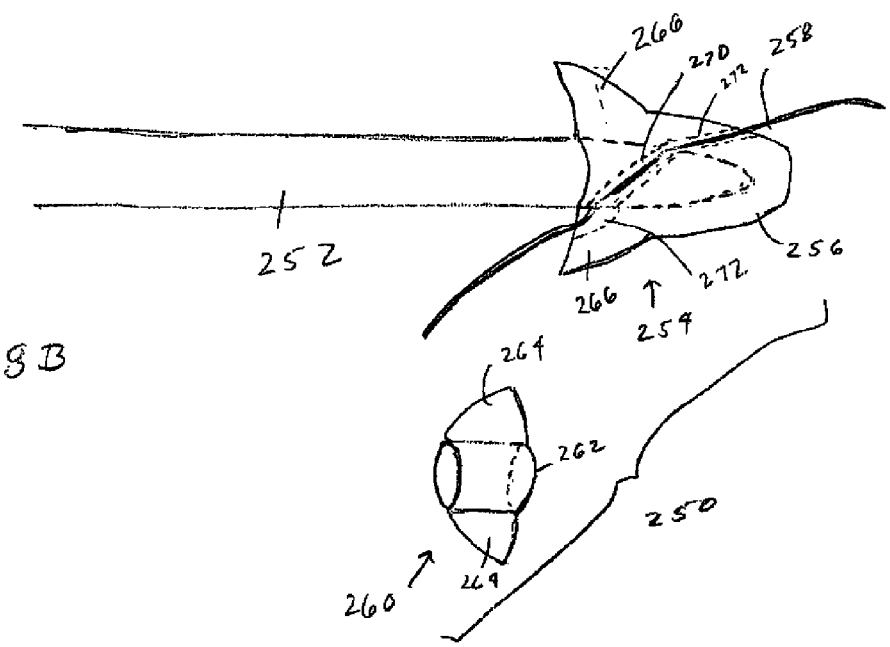

Yet another combination of insertion tool engaged with a self-fixating tip, and a guide engaged with the self-fixating tip, is at FIGS. 8A and 8B. In this embodiment, a guide is loosely engaged with the self-fixating tip, and is also loosely engages with the needle tip. The guide passes through an aperture of the self-fixating tip, through an aperture in the needle tip, and proximally through another aperture of the self-fixating tip. The insertion tool includes the aperture, as noted, and additionally includes a removable extension guard.

Referring to FIG. 8A, combination 250 includes an insertion tool that includes needle 252, needle tip 254, and a handle (not shown). Combination 250 additionally includes self-fixating tip 256, optional suture 258, and removable extension guard 260. Needle tip 254 includes aperture 270, within which guide 258 can be loosely engaged. Self-fixating tip 256 includes apertures 272, within which guide 258 can be loosely engaged.

Removable extension guard 260 includes tube 262 and extension guards 264. Tube 262 can be fitted over needle 252 and positioned proximal to needle tip 254 so extension guards 264 align behind lateral extensions 266 of self-fixating tip 256. This configuration is shown at FIG. 8A. In a second configuration, as shown at FIG. 8B, the insertion tool can be used without removable extension guard 260.

According to exemplary methods the configuration of FIG. 8A, including removable extension guard 260 installed on needle 252, can be used to initially place self-fixating tip 256 at tissue of the pelvic region. Without dis-engaging needle tip 254 from self-fixating tip 256, the position of self-fixating tip 256 can be adjusted to a tissue location of increased or decreased penetration. Needle 252 can be disengaged from the implanted self-fixating tip. The position of the implanted self-fixating tip or connected implant can be assessed to consider whether additional adjustment is desired. If so, removable extension guard 260 can be removed from needle 252 to result in the configuration of 8B. Needle tip 254 can be guided into re-engagement with self-fixating tip 256, and the insertion tool can be used to cause self-fixating tip to be inserted more deeply into the tissue.

An insertion tool as generally or specifically described herein can be used for initial placement of the self-fixating tip engaged with a guide. For this initial placement the guide need not be threaded through an aperture at a needle tip. Once the self-fixating tip is placed, the guide remains engaged within the self-fixating tip. In preferred embodiments, a proximal guide portion (non-marked) extends from the proximal end of the self-fixating tip, and a distal (marked) guide portion extends from the distal end of the self-fixating tip. Both guide portions can be placed external to the patient incision. The proximal guide portion is the portion that can be used to lead a needle tip to the self-fixating tip. If necessary or desired, the proximal guide portion can be threaded through an aperture of a needle tip and the needle tip can be guided along the proximal guide portion to the self-fixating tip that has been initially placed at tissue of the pelvic region. The insertion tool can be used to adjust the location of the self-fixating tip by moving the self-fixating tip in a direction of deeper penetration into the tissue.

Specific steps of embodiments of the described methods can include a method of treating a pelvic condition by providing a combination of an implant and a tool, as described. The implant includes a self-fixating tip and the needle tip includes an aperture that is capable of engaging a guide. The self-fixating tip and needle tip are designed to allow the needle tip to engage the self-fixating tip in a configuration that allows the needle to push the self-fixating tip for implanting the self-fixating tip in tissue of the pelvic region. Upon such engagement, the needle tip and self-fixating tip can be introduced into the pelvic region through an incision in a patient and the needle can be used to insert the self-fixating tip into tissue of the pelvic region. The particular placement of the self-fixating tip will depend on the type of condition being treated and the type of method being performed. Examples of tissue into which the self-fixating tip can be placed include tissue of the obturator foramen (e.g., obturator internus muscle), levator ani, coccygeous muscle, iliococcygeous muscle, arcus tendineus, sacrospinous ligament, tissue in a region of the ischial spine, etc.

According to such embodiments, the self-fixating tip can engage a guide, either in a fixed or a loose manner. The self-fixating tip can be engaged with the guide before the self-fixating tip is placed at the tissue of the pelvic region. This allows the guide to be available after the self-fixating tip is initially placed at a tissue location, so the guide can be used to find the self-fixating tip should the self-fixating tip require adjustment of location. In specific, a guide can engage a self-fixating tip by being threaded through an aperture in the self-fixating tip, or by being secured to the self-fixating tip. After the self-fixating tip is initially placed, a surgeon can assess the position of the self-fixating tip and the degree of support (of a tissue of the pelvic region) that is achieved compared to the degree of support that is desired. If adjustment of location of the self-fixating tip is desired the surgeon can use the guide to re-connect the needle tip with the initially-implanted self-fixating tip, and use the insertion tool to adjust the position of the self-fixating tip, e.g., to provide added support.

Exemplary steps of an embodiment of this method can include implanting (initially placing) a self-fixating tip, wherein the self-fixating tip is engaged with a guide. After checking for proper placement and deciding that adjustment of the initial location of the self-fixating tip is desired, the guide can be passed through an aperture of a needle tip. (Alternately, the guide can be passed through the aperture prior to initial placement of the self-fixating tip.) The needle tip can be moved along the guide to place the needle tip in contact with the self-fixating tip located in the pelvic tissue, to engage the self-fixating tip. The self-fixating tip can be moved deeper into the tissue to provide additional tension.

The guide can be bioresorbable, and may be left in place. Alternately, a guide that engages a self-fixating tip in a fixed manner can be severed as close as possible to the self-fixating tip to remove the guide after use. A guide that engages a self-fixating tip in a loose manner may be removed from the patient by pulling a loose end of the guide to remove the entire guide from the patient.

Other embodiments of methods of the present description include implanting (initially placing) a self-fixating tip, wherein the self-fixating tip includes one or more lateral extension and the insertion tool includes an extension guard that can correspond to each lateral extension. This embodiment does not require the use of a guide, and allows for adjustment of the initial placement of the self-fixating tip either to increase or decrease the penetration of the self-fixating tip. The needle tip is engaged with the self-fixating tip with each extension guard lining up proximal to a lateral extension of the self-fixating tip. The self-fixating tip is placed at tissue as desired, and can be checked for proper placement. If adjustment of the initial location of the self-fixating tip is desired, the tool may be used to move the self-fixating tip either to deeper tissue penetration or reduced tissue penetration, prior to dis-engaging the needle tip from the self-fixating tip. Adjustment can be performed until a desired location is achieved and the needle tip can be dis-engaged from the self-fixating tip.

According to yet other embodiments of methods, an implant may be placed using an insertion tool that includes an aperture at a needle tip, and a self-fixating tip that can be fixedly engaged with a guide. The guide is threaded through an aperture at a needle tip and the needle tip is placed within tissue of the pelvic region near the desired location of the self-fixating tip. A proximal guide portion (not engaged with the self-fixating tip) remains external to the patient and can be used to place traction on the guide and cause the self-fixating tip to penetrate tissue adjacent to the location of the needle tip; i.e., the self-fixating tip is pulled into tissue adjacent to the location of the needle tip. The method does not require engagement between the self-fixating tip and the needle tip in a manner that allows the insertion tool to push the self-fixating tip into tissue. See, e.g., FIG. 9.

Figure 9:
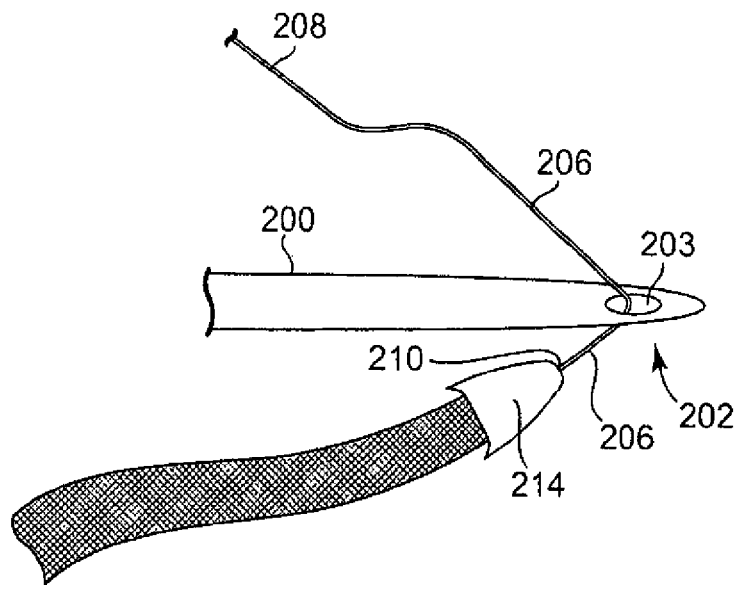
FIG. 9 illustrates an embodiment of a needle tip engaged with a guide, the guide also being engaged with a self-fixating tip of an implant.

FIG. 9 illustrates an embodiment of an insertion tool that includes an aperture at a needle tip, and an implant that includes a guide engaged with a self-fixating tip. Referring to FIG. 9, illustrated is a combination of an insertion tool that includes a needle tip that has an aperture, a self-fixating tip that is not designed to engage the needle tip, and a guide that is threaded through the aperture and fixedly engaged with the self-fixating tip. Insertion tool needle 200 includes needle tip 202. Needle tip 202 includes aperture 203, within which guide 206 is loosely engaged, i.e., threaded. Guide 206 includes proximal guide portion 208 and fixed distal guide end 210 attached to a distal end of self-fixating tip 214. Guide 206 is threaded through aperture 203 of needle tip 202 and, preferably, proximal guide portion 208 extends to a location external to a patient incision, allowing a user (e.g. surgeon) to grasp proximal guide portion 208 to place fraction on the guide. When needle tip 202 is placed within tissue of the pelvic region, traction at proximal guide portion 208 to pull proximal guide portion 208 in a proximal direction, causes self-fixating tip 214 to penetrate tissue adjacent to the location of needle tip 214.

Figure 10:
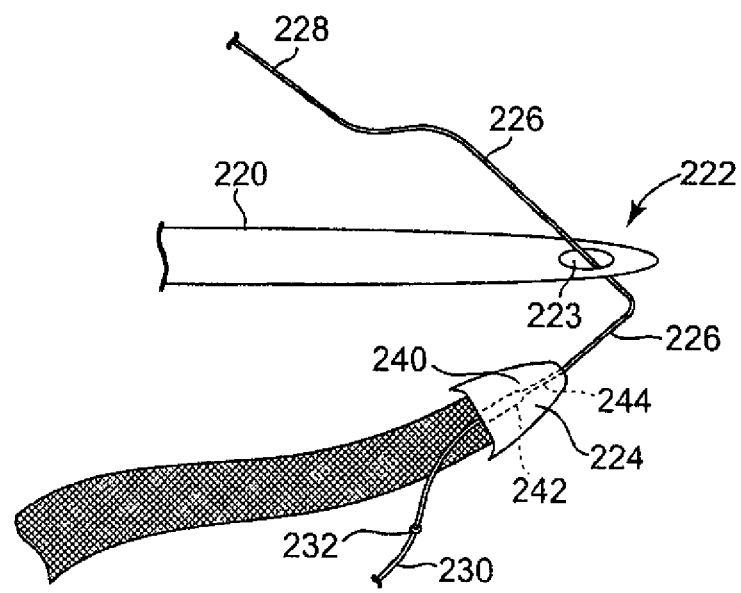
FIG. 10 illustrates an embodiment of a needle tip engaged with a guide, the guide also being engaged with a self-fixating tip of an implant.

An alternate embodiment is illustrated at FIG. 10, showing an insertion tool that includes an aperture at a needle tip, and an implant that includes a guide engaged with a self-fixating tip. Referring to FIG. 10, illustrated is a combination of an insertion tool that includes a needle tip that has an aperture, a self-fixating tip that is not designed to engage the needle tip, and a guide that is threaded through the needle tip aperture and is loosely engaged with the self-fixating tip but includes a structure that allows the guide to become fixedly engaged with the self-fixating tip to allow traction placed on the guide to place fraction on the self-fixating tip. Insertion tool needle 220 includes needle tip 222. Needle tip 222 includes needle tip aperture 223, within which guide 226 is loosely engaged, i.e., threaded. Guide 226 includes proximal guide portion 228 and distal guide portion 230, including enlargement 232. Guide 226 is threaded through aperture 223 of needle tip 222 and, preferably, proximal guide portion 228 extends to a location external to a patient incision, allowing a user (e.g. surgeon) to grasp the loose end and place traction on guide 226. Distal guide portion 230 passes through aperture 240 of self-fixating tip 224. Aperture 240 includes narrow portion 244 and wider portion 242. Enlargement 232 can pass through wider portion 242 but is too large to pass into narrow portion 244. When traction is applied to proximal guide portion 228, enlargement 232 is drawn into aperture 240 and becomes fixedly engaged with self-fixating tip 224, causing and the traction to become applied to self-fixating tip 214. When needle tip 222 is placed within tissue of the pelvic region, traction at proximal guide portion 228 to pull proximal guide portion 208 in a proximal direction, causes self-fixating tip 224 to penetrate tissue adjacent to the location of needle tip 222.

A method according to these embodiments can include use of an implant that includes a self-fixating tip at an end of an extension portion. A guide can be engaged with the self-fixating tip by being fixed to the self-fixating tip. Alternately the guide may be loosely threaded through an aperture in the self-fixating tip and may include an enlargement such as a knot or other structure that is of a size that is too large to slide through the aperture. The enlargement can be brought into contact with the aperture to allow the guide to pull the self-fixating tip.

The guide can be threaded through the aperture of the needle tip. The needle tip can be inserted into tissue in the pelvic region, leaving a proximal guide portion external to the patient. Traction can be applied at the proximal guide portion in a proximal direction to cause the self-fixating tip to penetrate tissue. By one method, the self-fixating tip can be caused to penetrate tissue with applied traction combined with movement of the needle tip, i.e., by placing traction on the guide and pushing the needle tip into tissue to cause the self-fixating tip to penetrate tissue. Alternately, the self-fixating tip can be caused to penetrate tissue with desired placement of the needle tip, maintaining a stationary position of the needle tip within tissue, and placing traction on the guide, e.g., pulling the guide proximally, to pull the self-fixating tip into the tissue, i.e., by placing the needle tip at a desired tissue location and then placing traction on the guide to cause the self-fixating tip to penetrate tissue.

Exemplary methods for treating pelvic floor disorders are discussed, e.g., in Applicants' copending International patent application number PCT/US2007/16760, filed Jul. 25, 2007. The implants, tools, and methods described herein can be applied to and used in conjunction with implants, tools, and methods of that patent application to treat pelvic floor disorders such as prolapse, incontinence (urinary and fecal incontinence), conditions of the perineal body, conditions of levator muscle (such as a component of levator muscle), conditions of the levator hiatus, and combinations of two or more of these. According to various embodiments, a surgical implant can be used to treat a pelvic condition wherein the method includes placing an implant in a manner that support tissue of the pelvic floor, including one or more of levator muscle, coccygeus muscle, iliococcygeus muscle, tissue of a perineal body, pubococcygeus muscle, etc., in a male or female. Placement of the implant can be by any incision and dissection route, with particular methods involving a vaginal incisions or an incision in the perirectal, perianal, or perineal regions. By any method, an embodiment of a tool can be used, as described, wherein the tool includes an aperture for use with a guide, an extension guard, or both.

Specific embodiments of methods of supporting tissue of the pelvic floor can include creating an incision that allows access to a region of tissue of the pelvic floor and providing a pelvic implant comprising a tissue support portion and a self-fixating tip. The implant is passed through the incision and a tissue support portion of the implant is placed at the region of pelvic floor tissue. The tissue support portion is positioned at the region of the pelvic floor tissue in a manner to cause the tissue support portion to support the tissue of the pelvic floor tissue. An insertion tool is used to place the self-fixating tip at tissue of the pelvic region. The insertion tool includes an aperture for engaging a guide, an extension guard, or both, as described herein. The insertion tool can be used to initially place the self-fixating tip, and the location of the self-fixating tip can then be adjusted as described herein, optionally using the guide to re-engage the needle tip with the self-fixating tip previously placed in the tissue.

The implant can be placed to contact pelvic tissue as desired, to support the tissue, and can be secured to the tissue to be supported, e.g., by suturing. The implant can additionally be secured, e.g., using a self-fixating tip as described herein, to soft (e.g., muscle, ligament, tendon) tissue of the pelvic region for additional support, such as to tissue including sacrotuberous ligament; sacrospinous ligament; anococcygeal ligament ("anococcygeal body ligament"); periostium of the pubic bone (e.g., in a region of the ischial tuberosity); pubourethral ligament; ischial spine (e.g., at a region of the ischial spine); ischial tuberosity; arcus tendineus (sometimes referred to as the "white line"), e.g., using a tissue path between levator ani muscle and obturator internus muscle and attached at the arcus tendineus; and obturator internus muscle. A method may additionally involve placement of one or more additional extension portion of an implant using a tissue path that leads to an external incision such as: by passing through tissue of the obturator foramen to pass through an external incision at the inner thigh; passing above the pubic bone to exit at a suprapubic incision; passing in a posterior direction to an external perirectal or perianal incision, e.g., past the coccyx bone. Additionally or alternately, a method may involve placement of an extension portion of an implant to bone or fascia, such as the sacrum or pubic bone, or fascia thereof.

Other exemplary methods for treating pelvic floor disorders are discussed, e.g., in Applicants' copending International patent application number WO 2007/097994 and International patent application number PCT/US071014120, filed Jun. 15, 2007, entitled SURGICAL IMPLANTS, TOOLS, AND METHODS FOR TREATING PELVIC CONDITIONS. Implants, tools, and methods described herein can be applied to and used in conjunction with implants, tools, and methods of that patent application to treat pelvic conditions such as incontinence (various forms such as fecal incontinence, stress urinary incontinence, urge incontinence, mixed incontinence, etc.), vaginal prolapse (including various forms such as enterocele, cystocele, rectocele, vault prolapse, etc.), among others. Embodiments of implants include a self-fixating tip at a distal end of one or more extension portions. The self-fixating tip can be placed at and secured within tissue of the pelvic region to support the implant. As an example, a self-fixating tip can be placed at tissue of the obturator foramen (this phrase referring to tissue that lies within or spans the obturator foramen, for example the obturator internus muscle, the obturator membrane, or the obturator externus muscle). Other tissue of the pelvic region can also be locations useful for implanting a self-fixating tip. The self-fixating tips can be designed to engage a distal end of an insertion tool to allow the insertion tool to place the self-fixating tip at a desired tissue location by pushing.

Based on such methods, a method of the present description can include providing an implant sling comprising two self-fixating tips. Each self-fixating tip includes a base having a proximal base end and a distal base end. The proximal base end is connected to an extension portion of the implant. Optionally and preferably, two lateral extensions extend from the base. A tool is provided for extending from a vaginal incision to an obturator foramen. The method includes creating only a single vaginal incision, dissecting to vaginal tissue to be supported, and contacting a tissue support portion with vaginal tissue to be supported. The implant is inserted into the pelvic region through the vaginal incision. A first self-fixating tip is implanted at an obturator foramen on one side of the patient by using the needle, through the vaginal incision, to cause the self-fixating tip to penetrate tissue of the obturator foramen. A second self-fixating tip is implanted at an obturator foramen on an opposing side of the patient, again through the vaginal incision.

Implanting either or both of the first and second self-fixating tip can include passing the guide through an aperture of the first self-fixating tip, the second self-fixating tip, or both of these. An insertion tool comprising a needle is then used to place the self-fixating tip at tissue of the pelvic region. The needle is removed from the self-fixating tip. The guide extending through the self-fixating tip includes a proximal guide portion that extends to the proximal side of the self-fixating tip. A second portion of the guide can include an end that is fixed to the self-fixating tip or may extend loosely through the self-fixating tip as a distal guide portion. The proximal guide portion and the distal guide portion (if present) can remain external to the incision. The proximal guide portion is passed (threaded) through the aperture in the needle tip (this may be done before or after implantation of a self-fixating tip). The aperture at the needle tip is moved from along the proximal guide portion to the implanted self-fixating tip and engages self-fixating tip previously inserted in the tissue. The needle can then be used to adjust the location of the self-fixating tip by causing the self-fixating tip to be penetrated more deeply into the tissue. This adjustment step may be done for one or both of the self-fixating tips of this exemplary method. For placement and adjustment of an implant that includes fewer or more than a two self-fixating tips, any number of self-fixating tips can be adjusted.

The invention relates to combinations of tools, implants, and optional guide as described, including combinations specifically described or otherwise. A combination may include an implant that includes a self-fixating tip, an optional guide, and one or more insertion tool. A combination may include a single insertion tool, or two or more insertion tools, which may be the same or different. For example, a combination may include multiple insertion tools that include the same or various curves, for placement of different self-fixating tips of an implant at different positions of the pelvic region.

A combination may, alternately or in addition, include two or more insertion tools having different needle tips; one insertion tool may include a needle tip that includes an aperture and a second insertion tool may include a needle tip that includes no aperture but does include an extension guard. This combination of tools may additionally be combined with an implant that includes a self-fixating tip that is capable of being engaged with a guide and that includes at least one lateral extension. A first insertion tool, including a needle tip that includes an extension guard, may be used to implant a self-fixating tip and (before dis-engaging the insertion tool) the insertion tool may be used to adjust the implant to increase or decrease tissue penetration. Subsequently, a second insertion tool, including an aperture at the needle tip, may be guided along the suture to the self-fixating tip placed at tissue and the position of the self-fixating tip can be further adjusted by increasing tissue penetration. Optionally, a single insertion tool can include an aperture capable of engaging a guide and a removable extension guard, and can be used in both steps, first including the extension guard and later without the extension guard.

Although the invention has been described in terms of particular embodiments and applications, one of ordinary skill, in light of this teaching, can generate additional embodiments and modifications without departing from the spirit of or exceeding the scope of the claimed invention. Accordingly, it is to be understood that the drawings and descriptions herein are presented by way of example to facilitate comprehension of the invention and should not be construed to limit the scope thereof.

Following is a description of an exemplary method of implanting a urethral sling to treat female incontinence, using a tool, method, and implant as described herein. The sling ("Sling") is a mesh strip that includes a self-fixating tip at each end. A midline mark is located at the middle of the sling based on the length of the sling between the self-fixating tips ("Sling Tips"). The needle engages the self-fixating tips to allow the self-fixating tips to be pushed into tissue. The needle includes a curve in two dimensions and has a needle tip that has an aperture that engages a guide. The needle includes a mark (groove) at the shaft that corresponds to the urethra when the needle tip is approximately located at a location for implanting a self-fixating tip at an obturator foramen. The self-fixating tips engage the needle tip and also include an aperture that allows the guide to be threaded through the self-fixating tip and the needle tip while the needle tip engages the self-fixating tip.

Patient Preparation
1. Patient should be placed in a modified dorsal lithotomy position with hips flexed, legs elevated in stirrups, and buttocks even with the edge of table.
2. Ensure the bladder is empty. A catheter is not required but may aid in identifying the urethra during the procedure.
3. Place a weighted vaginal retractor or other suitable vaginal refraction, if desired.
4. Ensure that a 2-0 monofilament polypropylene suture at least 18" (46 cm) long is available, needle removed.

Incision and Dissection
5. On the anterior wall of the vagina, draw a mark to identify the location of a suburethral incision approximately at the level of the mid-urethra. Variations may occur in specific incisions due to individual technique and patient anatomy.
6. Infiltrate incision site with saline if desired.
7. Place an Allis forceps on the incision margin to expose the incision.
8. Incise the vaginal wall. The incision should be approximately 1.5 cm in length.
9. Insert the tip of a Metzenbaum scissors laterally, spread and advance the scissors until the tip of the scissors touches the posterior portion of the ischiopubic ramus (about 1-1.5 cm). Do this bilaterally.
10. The subsequent dissection and needle insertion orientation can be visualized by first palpating the edge of the ischiopubic ramus beginning at the level of the vaginal incision; continue palpating the edge of the bone moving cephalad toward the level of the clitoris and note where the adductor longus tendon inserts into the pubic ramus. The dissection and needle insertion should be aimed just inferior to this location, lateral to the bony edge.

Placing the Sling Mesh

11. Tie a knot near one end of the suture (approx. 5 cm) and thread the other end through one of the Sling Tips. The suture should be drawn through the Sling Tip until ½ of the length has passed. The knotted end should be distal to the Sling Tip.
12. Insert the unknotted end of the suture that is passing out of the proximal end of the Sling Tip into the hole (aperture) in the end of the needle tip.

NOTE: The tip of the needle passer is keyed to the Sling Tip to prevent rotation during placement.

13. Assemble the Sling onto the needle by sliding the Sling Tip onto the needle tip.
14. While assembling, ensure that the Sling Tip is oriented such that the mesh wraps along the outside of the needle bend.

NOTE: Ensure that both suture ends are visible during placement of the Sling Tip.

15. Insert the needle/Sling assembly into the vaginal incision. Track the needle along the posterior surface of the ischiopubic ramus until the mark at the midline on the mesh is approximately at the midline position under the urethra.
16. Remove the needle leaving the suture in position.
17. Place the second Sling Tip onto the needle tip. To ensure that the mesh lies flat under the urethra, verify that the Sling is not twisted.
18. Insert the needle/Sling assembly through the vaginal incision, into the patient's contralateral side. Track the needle along the posterior surface of the ischiopubic ramus until appropriate Sling tension under the urethra is achieved.
19. Remove the needle and assess the Sling tension.
20. If desired, more tension can be added by advancing the first Sling Tip.
    a. To add tension, guide the needle back to the first Sling Tip using the suture.
    b. Thread the suture through the hole in the end of the needle tip.
    c. Pull the suture just tight enough to remove any slack.
    d. Advance the needle along the suture toward the Sling Tip.

NOTE: The needle tip is approaching the Sling Tip when the groove on the needle is approaching the urethra.

e. Once needle tip is engaged with the Sling Tip, advance the Sling Tip until the desired tension is achieved.
    f. Remove the needle leaving the suture in position.
    g. Assess the tension again. More tension can be added by repeating Steps 20 *a-f*.
21. When the desired tension is achieved, remove the suture by gently pulling the knotted suture end.
22. Cystoscopy is not required, but may be performed at this point.
23. Complete the closure of the vaginal incision.

The invention claimed is:

1. In combination, an insertion tool and an implant, the implant comprising a support portion, an extension portion, and a self-fixating tip connected to the extension portion, the self-fixating tip comprising an aperture, the insertion tool comprising:
   a handle and a needle extending from the handle, the needle comprising a needle shaft having a proximal end attached to the handle and a distal end that includes a needle tip, the needle tip comprises an aperture that allows passage of a guide and guided relative movement of the needle tip along the guide,
   wherein the needle tip engages the fixating tip to allow the needle to push the self-fixating tip for surgical implantation,
   wherein, when the needle tip engages the self-fixating tip, the guide can pass through the aperture of the needle and the aperture of the self-fixating tip, and
   wherein the aperture of the needle exits a surface of the needle shaft at a location distal to the needle shaft proximal end.

2. The combination of claim 1 wherein the aperture of the needle includes a bore having a diameter in the range from 0.1 to 2 millimeters.

3. The combination of claim 1 wherein the needle tip comprises a needle end, the aperture of the needle comprises a longitudinal bore extending from the needle tip end into the needle tip, and a channel extending from the bore further along a surface of the needle tip.

4. The combination according to claim 1 wherein the self-fixating tip comprises a base comprising a proximal base end and a distal base end, the proximal base end being connected to the extension portion, the base comprising the aperture of the self-fixating tip extending from the proximal base end through the base to the distal base end, and a lateral extension extending from the base.

5. The combination according to claim 4 wherein the insertion tool includes an extension guard at the distal end that, when the needle tip engages the self-fixating tip to allow the needle to push the self-fixating tip for surgical installation, the extension guard is located proximal to the lateral extension and reduces the force required to move the self-fixating tip in a proximal direction through muscle tissue.

6. A method of preparing an assembly for surgical treatment, the method comprising:
   providing the combination according to claim 1,
   providing the guide engaged with the self-fixating tip,
   engaging the self-fixating tip with the needle tip in a configuration that allows the needle to push the self-fixating tip, and
   passing the guide through the aperture in the needle tip.

7. A method of treating a pelvic condition, the method comprising:
   providing the combination according to claim 1, engaging the self-fixating tip with the needle tip in a configuration that allows the needle to push the self-fixating tip, inserting the needle tip and self-fixating tip through an incision in a patient into a pelvic region, and using the needle to insert the self-fixating tip into tissue of the pelvic region.

8. A method according to claim 7, the method comprising providing the guide engaged with the self-fixating tip,
   passing the guide through the aperture of the self-fixating tip and the aperture of the needle tip,
   after using the needle to insert the self-fixating tip into tissue of the pelvic region, then removing the needle from the self-fixating tip,
   leaving an end of the guide external to the incision,
   placing the guide through the aperture in the needle tip, and
   guiding the aperture of the needle tip along the guide and engaging the needle tip with the self-fixating tip previously inserted in the tissue.

9. A method according to claim 8 comprising,
   after guiding the aperture of the needle tip along the guide to place the needle tip in contact with the self-fixating tip located in the pelvic tissue,
   using the needle to cause the self-fixating tip to penetrate further into the tissue.

10. A method of treating a pelvic condition, the method comprising
- providing the combination according to claim 1, wherein the implant comprises a urethral sling comprising the extension portion, a second extension portion, the self-fixating tip, a second self-fixating tip, each self-fixating tip comprising
  - a base comprising a proximal base end and a distal base end, the proximal base end being connected to one of the two extension portions, and
  - two fixed lateral extensions extending from the base,
- creating a single medial incision in a male or female anatomy,
- dissecting toward tissue to be supported,
- contacting the support portion of the implant with tissue to be supported,
- implanting the self-fixating tip at an obturator foramen on one side of the patient by using the needle to cause the self-fixating tip to penetrate tissue of the obturator foramen,
- implanting the second self-fixating tip at an obturator foramen on an opposing side of the patient by using the needle to cause the second self-fixating tip to penetrate tissue of the obturator foramen, wherein the first self-fixating tip, the second self-fixating tip, or both, is implanted by:
- providing the guide,
- passing the guide through the aperture of the self-fixating tip,
- using the needle to cause the self-fixating tip to penetrate tissue of the pelvic region and removing the needle from the self-fixating tip,
- leaving an end of the guide external to the incision,
- passing the guide through the aperture in the needle tip, and
- guiding the aperture of the needle tip along the guide and engaging the needle tip with the self-fixating tip previously inserted in the tissue.

11. The method of claim 10 comprising
- after guiding the aperture of the needle tip along the guide to engage the needle tip with the self-fixating tip previously inserted in the tissue, using the needle to cause the self-fixating tip to penetrate further into the tissue.

12. A method according to claim 10 comprising placing the self-fixating tip at tissue of a right obturator foramen, and placing the second self-fixating tip at tissue of a left obturator foramen.

13. In combination, an insertion tool and an implant,
- the implant comprising a support portion, an extension portion, and a self-fixating tip connected to the extension portion,
- the insertion tool comprising a handle and a needle extending from the handle, the needle comprising a needle shaft having a proximal end attached to the handle and a distal end that includes a needle tip, the needle tip comprises an aperture that allows guided relative movement of the needle tip along a guide, wherein the aperture exits a surface of the needle shaft at a location distal to the needle shaft proximal end,
wherein the self-fixating tip engages the needle tip to allow the needle to push the self-fixating tip for surgical implantation, and
wherein the self-fixating tip comprises a base comprising a proximal base end and a distal base end, the proximal base end being connected to the extension portion, the base comprising a base aperture extending from the proximal base end through the base to the distal base end, and a lateral extension extending from the base.

14. A method of treating a pelvic condition, the method comprising providing an insertion tool and an implant,
- the implant comprising a support portion, an extension portion, and a self-fixating tip connected to the extension portion,
- the insertion tool comprising a handle and a needle extending from the handle, the needle comprising a needle shaft having a proximal end attached to the handle and a distal end that includes a needle tip, the needle tip comprises an aperture that allows guided relative movement of the needle tip along a guide, wherein the aperture exits a surface of the needle shaft at a location distal to the needle shaft proximal end,
- engaging the self-fixating tip with the needle tip in a configuration that allows the needle to push the self-fixating tip,
- inserting the needle tip and self-fixating tip through an incision in a patient into a pelvic region, and using the needle to insert the self-fixating tip into tissue of the pelvic region,
- providing a guide and passing the guide through an aperture of the self-fixating tip,
- using the needle to insert the self-fixating tip into tissue of the pelvic region and then removing the needle from the self-fixating tip,
- leaving an end of the guide external to the incision,
- placing the guide through the aperture in the needle tip, and
- guiding the aperture of the needle tip along the guide and engaging the needle tip with the self-fixating tip previously inserted in the tissue.

15. A method according to claim 14 comprising,
- after guiding the aperture of the needle tip along the guide to place the needle tip in contact with the self-fixating tip located in the pelvic tissue,
- using the needle to cause the self-fixating tip to penetrate further into the tissue.

16. A method of treating a pelvic condition, the method comprising
- providing a combination comprising an insertion tool and an implant,
  - the implant comprising a urethral sling comprising a support portion, a first extension portion, a second extension portion, a first self-fixating tip connected to the first extension portion, and a second self-fixating tip connected to the second extension portion,
  - the insertion tool comprising a handle and a needle extending from the handle, the needle comprising a needle shaft having a proximal end attached to the handle and a distal end that includes a needle tip, the needle tip comprises an aperture that allows guided relative movement of the needle tip along a guide, wherein the aperture exits a surface of the needle shaft at a location distal to the needle shaft proximal end,
  - the two self-fixating tips each comprising
    - a base comprising a proximal base end and a distal base end, the proximal base end being connected to one of the extension portions, and
    - two fixed lateral extensions extending from the base, the method comprising:
- creating a single medial incision in a male or female anatomy,
- dissecting toward tissue to be supported,
- contacting the support portion of the implant with tissue to be supported, implanting the first self-fixating tip at an obturator foramen on one side of the patient by using the needle to cause the self-fixating tip to penetrate tissue of the obturator foramen, implanting the second self-fixating tip at an obturator foramen on an opposing side of the patient by using the needle to cause the self-fixating tip to penetrate tissue of the obturator foramen, wherein the first self-fixating tip, the second self-fixating tip, or both, is implanted by:

providing a guide, passing the guide through an aperture of the self-fixating tip, using the needle to cause the self-fixating tip to penetrate tissue of the pelvic region and removing the needle from the self-fixating tip, leaving an end of the guide external to the incision, passing the guide through the aperture in the needle tip, and guiding the aperture along the guide and engaging the needle tip with the self-fixating tip previously inserted in the tissue.

17. The method of claim 16 comprising after guiding the aperture along the guide to engage the needle tip with the self-fixating tip previously inserted in the tissue, using the needle to cause the self-fixating tip to penetrate further into the tissue.

18. A method of treating a pelvic condition, the method comprising providing a combination comprising an insertion tool and an implant, the implant comprising a urethral sling comprising a support portion, an extension portion, and a self-fixating tip connected to the extension portion, the insertion tool comprising a handle and a needle extending from the handle, the needle comprising a needle shaft having a proximal end attached to the handle and a distal end that includes a needle tip, the needle tip comprises an aperture that allows guided relative movement of the needle tip along a guide, wherein the aperture exits a surface of the needle shaft at a location distal to the needle shaft proximal end, providing a guide engaged with the self-fixating tip, passing the guide through an aperture of the self-fixating tip, engaging the self-fixating tip with the needle tip in a configuration that allows the needle to push the self-fixating tip, inserting the needle tip and self-fixating tip through an incision in a patient into a pelvic region then removing the needle from the self-fixating tip, leaving an end of the guide external to the incision, placing the guide through the aperture in the needle tip, and guiding the aperture along the guide and engaging the needle tip with the self-fixating tip previously inserted in the tissue.

19. A method according to claim 18 comprising placing the self-fixating tip at tissue of a right obturator foramen, and placing a second self-fixating tip at tissue of a left obturator foramen.

* * * * *